US009665935B2

(12) United States Patent
Yamato et al.

(10) Patent No.: US 9,665,935 B2
(45) Date of Patent: May 30, 2017

(54) IMAGE PROCESSING DEVICE AND PROGRAM

(71) Applicant: Konica Minolta Inc., Tokyo (JP)

(72) Inventors: Hiroshi Yamato, Amagasaki (JP); Kenta Shimamura, Takatsuki (JP); Osamu Toyama, Kakogawa (JP); Shintaro Muraoka, Hachioji (JP); Sho Noji, Kokubunji (JP)

(73) Assignee: KONICA MINOLTA, INC., Tokyo (JP)

( * ) Notice: Subject to any disclaimer, the term of this patent is extended or adjusted under 35 U.S.C. 154(b) by 34 days.

(21) Appl. No.: 14/891,110

(22) PCT Filed: Apr. 9, 2014

(86) PCT No.: PCT/JP2014/060287
§ 371 (c)(1),
(2) Date: Nov. 13, 2015

(87) PCT Pub. No.: WO2014/185197
PCT Pub. Date: Nov. 20, 2014

(65) Prior Publication Data
US 2016/0098836 A1    Apr. 7, 2016

(30) Foreign Application Priority Data

May 16, 2013    (JP) ................. 2013-104336

(51) Int. Cl.
*G06K 9/00* (2006.01)
*G06T 7/00* (2017.01)
(Continued)

(52) U.S. Cl.
CPC .............. *G06T 7/0012* (2013.01); *A61B 6/50* (2013.01); *A61B 6/5217* (2013.01);
(Continued)

(58) Field of Classification Search
CPC .................................................. G06T 7/0012
See application file for complete search history.

(56) References Cited

U.S. PATENT DOCUMENTS

| 7,421,101 B2* | 9/2008 | Georgescu | G06T 7/20 |
| | | | 382/103 |
| 2007/0260137 A1* | 11/2007 | Sato | G06T 5/50 |
| | | | 600/407 |
| 2011/0194748 A1* | 8/2011 | Tonomura | A61B 5/0048 |
| | | | 382/131 |

FOREIGN PATENT DOCUMENTS

| JP | 3574301 B2 | 7/2004 |
| JP | 2004312434 A | 11/2004 |

(Continued)

OTHER PUBLICATIONS

X. Xu, et al; Image feature analysis for computer-aided diagnosis: accurate determination of . . . ; Med. Phys., vol. 22; No. 5; May 1995; pp. 617-626.

(Continued)

*Primary Examiner* — Oneal R Mistry
(74) *Attorney, Agent, or Firm* — Lucas & Mercanti, LLP

(57) ABSTRACT

An object of the present invention is to provide an image processing technology capable of perceiving a motion of the shape of a target area. An image processing device (3) according to the present invention includes: a dynamic image acquiring unit (110) that acquires a dynamic image; a boundary line extracting means (130) that acquires a plurality of target area boundary lines by extracting boundary lines of a target area; a displacement correcting means (140) that acquires a predetermined number of displacement-corrected boundary lines in which a removal-required component is removed by calculating a displacement amount, which is the removal-required component, using a base boundary line as a displacement base for one or more of (Continued)

target area boundary lines other than the base boundary line among the plurality of target area boundary lines by using pixels corresponding to the plurality of target area boundary lines and correcting a predetermined number of the target area boundary lines other than the base boundary line by using the displacement amount after the calculation of the displacement amount; and a display means (34) that displays displacement-corrected boundary line information for display based on the predetermined number of displacement-corrected boundary lines.

20 Claims, 23 Drawing Sheets

(51) Int. Cl.
    *A61B 6/00*     (2006.01)
    *G06K 9/46*     (2006.01)
    *G06K 9/62*     (2006.01)
    *G06T 7/20*     (2017.01)
    *G06T 5/00*     (2006.01)
    *G06T 5/50*     (2006.01)
(52) U.S. Cl.
    CPC .......... *A61B 6/5288* (2013.01); *G06K 9/0053* (2013.01); *G06K 9/00536* (2013.01); *G06K 9/4604* (2013.01); *G06K 9/6215* (2013.01); *G06K 9/6267* (2013.01); *G06T 5/001* (2013.01); *G06T 5/50* (2013.01); *G06T 7/20* (2013.01); *G06K 2009/4666* (2013.01); *G06T 2207/10116* (2013.01); *G06T 2207/30048* (2013.01); *G06T 2207/30061* (2013.01)

(56) References Cited

FOREIGN PATENT DOCUMENTS

| | | |
|---|---|---|
| JP | 2009172190 A | 8/2009 |
| JP | 2010069099 A | 4/2010 |
| JP | 2010245707 A | 10/2010 |
| WO | 2006137294 A1 | 12/2006 |
| WO | 2013191961 A1 | 12/2013 |

OTHER PUBLICATIONS

H. Aoki, et al; Unrestrained respiration monitoring for sleeping person using fiber grating . . . ; Institute of Electronics, Information and Communication Engineers; 2001; pp. 320-321.

N. Nakamori, et al; Image feature analysis and computer-aided diagnosis in digital radiography: automated . . . ; Med. Phys.; vol. 17; No. 3; May 1990; pp. 342-350.

International Search Report dated Jul. 22, 2014 for PCT/JP2014/060287 and English translation.

* cited by examiner

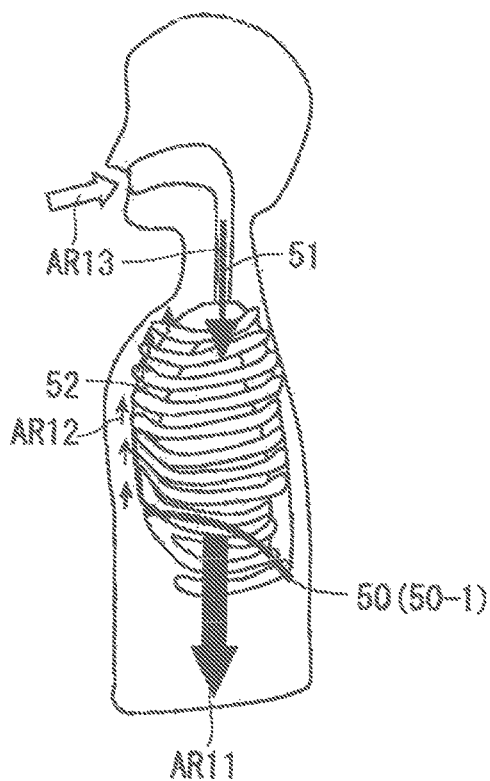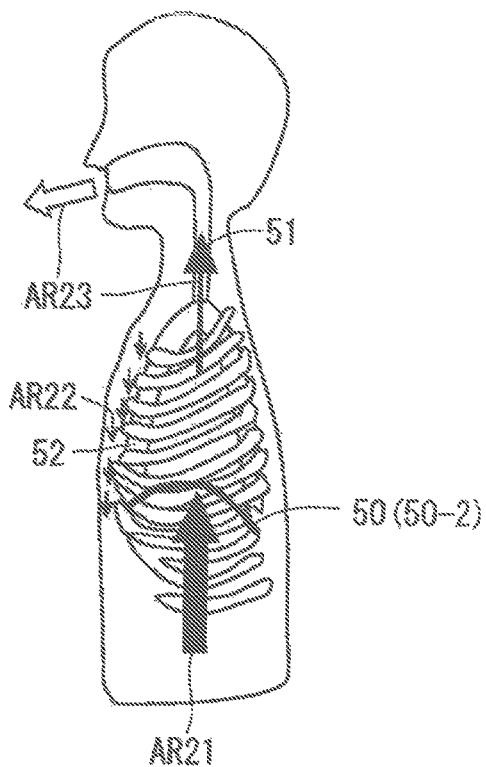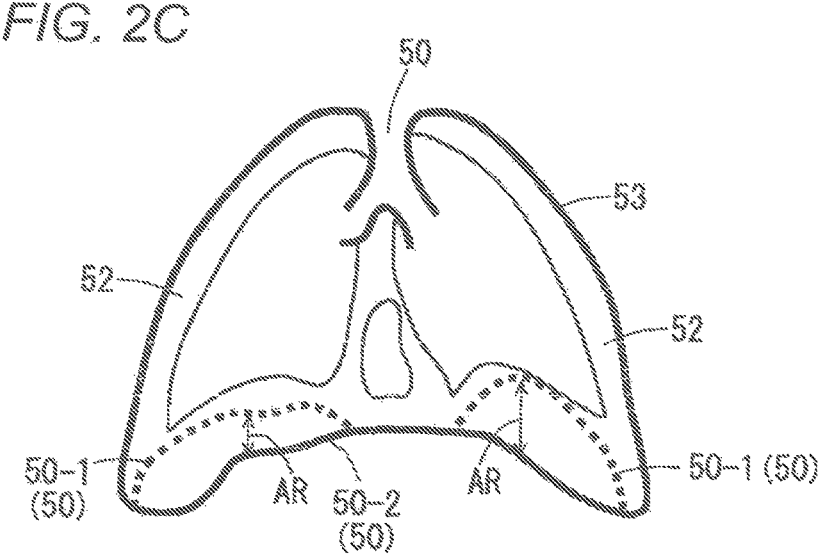

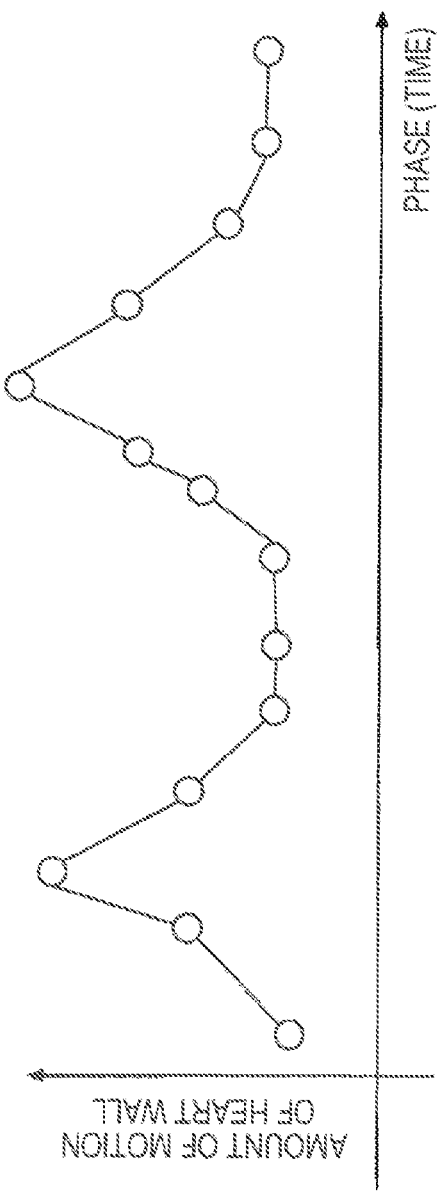

IMAGE PROCESSING DEVICE AND PROGRAM

CROSS REFERENCE TO RELATED APPLICATION

This Application is a 371 of PCT/JP2014/060287 filed on Apr. 9, 2014 which, in turn, claimed the priority of Japanese Patent Application No. JP2013-104336 filed on May 16, 2013, both applications are incorporated herein by reference.

TECHNICAL FIELD

The present invention relates to an image processing technology of a dynamic image acquired by photographing a human body or an animal body.

BACKGROUND ART

At medical sites, by photographing an affected part included in an internal organ, a skeleton, or the like by using an X ray or the like, various tests and diagnoses are made. In recent years, by applying digital technologies, a dynamic image (an image group configured by a plurality of frame images) in which a motion of an affected part is acquired by using an X ray or the like can be acquired relatively easily.

Thus, since a dynamic image of a subject area including a diagnosis target area can be acquired by using a semiconductor image sensor such as a flat panel detector (FPD), a pathological analysis and a diagnosis based on a motion analysis of a diagnosis target area or the like, which cannot be performed according to conventional still-image photographing and analysis using X-ray photographing, have been attempted. Particularly, in a dynamic-state analysis of a chest X-ray, supports for a diagnosis/treatment (CAD for an X-ray dynamic image) using a functional and quantitative analysis of a dynamic-state relating to a change in the density of the inside of a pulmonary field for each position inside the pulmonary field have been also reviewed.

As a method for the quantitative analysis described above, a technology has been proposed in which analysis information effective for a diagnosis is generated by analyzing a temporal change based on frame images of a dynamic-state image of the chest.

For example, in a technology disclosed in Patent Literature 1, the technology has been disclosed which generates a new image by continuously acquiring a plurality of X-ray images in a time series, setting a line at a desired position for each of the plurality of X-ray images, acquiring a pixel row aligned along the set line, and aligning acquired pixel rows in the order of a time series.

In addition, in a technology disclosed in Patent Literature 2, the technology for acquiring a moving amount by measuring the position of the diaphragm based on a dynamic image, acquiring relative ventilation information for each divided chest area by specifying a dynamic image at the time of maximal inhalation and a dynamic image at the time of maximal exhalation and using a pixel differential value, executing linear interpolation between CT images, generating a coronal image, a sagittal image, and a Raysum image, measuring the position of the diaphragm based on the Raysum image, executing position adjustment between frames of the dynamic images of which the respiratory levels match those of the CT images and the Raysum image generated based on the CT images, and overlapping the ventilation information with the coronal image and the dynamic image has been disclosed. In addition, a method for measuring the positions of the horizontal diaphragm and a pulmonary apex, acquiring a moving amount, and displaying the graph of the motion based on the moving amount has been disclosed.

CITATION LIST

Patent Literatures

Patent Literature 1: JP 2004-312434 A
Patent Literature 2: WO 2006/137294 A

SUMMARY OF INVENTION

Technical Problem

However, while a diagnosis image represented using the method disclosed in Patent Literature 1 represents a change in the time direction in a fixed line as one cross-sectional image, the motion of the shape of a target area in the time direction (in other words, a temporal change of a two-dimensional space on a frame image) cannot be represented.

Meanwhile, also in Patent Literature 2, while the method for measuring specific positions of the horizontal diaphragm and the pulmonary apex, acquiring moving amounts (displacement amounts) at the positions, and displaying the motions at the positions based on the moving amounts has been disclosed, and a motion of the target area can be represented in one dimension, the motion of the two-dimensional shape of the target area cannot be represented.

In other words, according to the technologies disclosed in Patent Literatures 1 and 2, the temporal change of the two-dimensional space on the frame image cannot be acquired, and thus, the motion of the shape of the target area cannot be acquired.

The present invention is in consideration of such situations, and an object thereof is to provide an image processing technology capable of acquiring the motion of the shape of a target area desired by a user.

Solution to Problem

In order to solve the above problem, an image processing device which is an invention of claim 1 includes: a dynamic image acquiring means that acquires a dynamic image configured by a plurality of frame images acquired by sequentially photographing a time-varying physical state of a target area inside a human body or an animal body in a time direction; a boundary line extracting means that executes a boundary line extracting process in which a plurality of target area boundary lines are acquired by extracting boundary lines of the target area for a plurality of frame images among the plurality of frame images; a displacement correcting means that acquires a predetermined number of displacement-corrected boundary lines in which a removal-required component is removed by executing a displacement amount calculating process in which a displacement amount, which is the removal-required component, is calculated using a base boundary line as a displacement base for one or more of target area boundary lines other than the base boundary line among the plurality of target area boundary lines by using pixels corresponding to the plurality of target area boundary lines and executing a correction process in which a predetermined number of the target area boundary lines other than the base boundary line are corrected by using the displacement amount after the displacement amount calculating process; and a display means that displays displacement-corrected boundary line information for display based on the predetermined number of displacement-corrected boundary lines.

Further, an invention of claim 2 is the image processing device according to claim 1, wherein the removal-required component includes at least one component among deformation components according to a vertical motion, a parallel motion, and rotation in the target area.

Further, an invention of claim 3 is the image processing device according to claim 1 or 2, further including a frame selecting means that executes a frame selecting process including a process of selecting a base frame image used for extracting the base boundary line and a reference frame image used for extracting the target area boundary lines other than the base boundary line for selection target frame images including at least the plurality of frame images, wherein the displacement amount calculating process includes a process of calculating a displacement amount between corresponding pixels of the target area boundary line of the base frame image as the base boundary line and the target area boundary line of the reference frame image.

Further, an invention of claim 4 is the image processing device according to claim 3, wherein the selection target frame images include frame images photographed in the past in time with respect to the plurality of frame images, and the frame selecting process includes a process of selecting a frame image photographed for the same body in the past in time with respect to the plurality of frame images as the base frame image.

Further, an invention of claim 5 is the image processing device according to claim 3, further including a period classifying means that detects a target area period in which a periodical change of the target area of the body synchronized with photographing time at which the plurality of frame images are photographed occurs and classifies the plurality of frame images in units of the target area periods, wherein the base frame image and the reference frame image are frame images when the target area periods are within a same period, a value representing a time-varying physical state of the target area is defined as a physical state value, and the frame selecting process includes a first selection process selecting one frame image as the base frame image from among (b1) a frame image when the physical state value corresponds to a first set value set in advance, (b2) a frame image when the physical state value corresponds to a maximum value, and (b3) a frame image when the physical state value corresponds to a minimum value, and a second selection process selecting one frame image as the reference frame image from among (c1) a frame image when the physical state value corresponds to a second set value set in advance, (c2) a frame image that is adjacent to the base frame image in time, (c3) a frame image corresponding to the minimum value of the physical state value when the base frame image is the frame image of (b2), and (c4) a frame image corresponding to the maximum value of the physical state value when the base frame image is the frame image of (b3).

Further, an invention of claim 6 is the image processing device according to claim 3, wherein the displacement amount used for the correction process is a displacement amount between corresponding pixels of the base boundary line and one of the target area boundary lines, and the target area boundary lines other than one of the target area boundary lines are corrected using the displacement amount.

Further, an invention of claim 7 is the image processing device according to claim 3, wherein the displacement amount used for the correction process is a displacement amount from the target area boundary line nearest in time from the target area boundary line that is a correction target.

Further, an invention of claim 8 is the image processing device according to claim 3, wherein the displacement amount used for the correction process is a displacement amount between the base boundary line and the target area boundary line, which is the correction target, that is acquired as a sum of displacement amounts of two boundary lines adjacent in time.

Further, an invention of claim 9 is the image processing device according to any one of claims 1 to 8, further including an image generating means that generates a predetermined number of separate images separated for each predetermined number of displacement-corrected boundary lines, wherein the display means sequentially displays the predetermined number of separate images as displacement-corrected boundary line information.

An invention of claim 10 is the image processing device according to any one of claims 1 to 9, further including an image generating means that generates one still image such that the plurality of displacement-corrected boundary lines are displayed in an overlapping manner, wherein the display means displays the still image as the displacement-corrected boundary line information.

Further, an invention of claim 11 is the image processing device according to any one of claims 1 to 10, wherein the target area includes at least one of a diaphragm area and a heart area.

Further, an invention of claim 12 is a program that causes a computer to serve as the image processing device according to any one of claims 1 to 11 by being executed by the computer included in the image processing device.

Advantageous Effects of Invention

According to an image processing device disclosed in claims 1 to 11, a displacement amount calculating process is executed in which a displacement amount is calculated using a base boundary line as a displacement base for one or more of target area boundary lines other than a base boundary line among a plurality of target area boundary lines by using pixels corresponding to the plurality of target area boundary lines, and the displacement amount is a removal-required component. Then, a correction process is executed in which a predetermined number of the target area boundary lines other than the base boundary line are corrected by using the displacement amount after the displacement amount calculating process, whereby a predetermined number of displacement-corrected boundary lines in which a removal-required component is removed are acquired. Displacement-corrected boundary line information for display based on the predetermined number of displacement-corrected boundary lines is displayed. In other words, by displaying the displacement-corrected boundary lines acquired by removing the deformation corresponding to the displacement amount from the target area boundary lines, the user perceives a change in the shape of the target area boundary line, whereby the motion of the shape of the target area can be perceived. In addition, since the shape of the target area boundary line can be perceived, a partial abnormality of the shape can be found, and the partial abnormality such as adhesion can be easily diagnosed. Furthermore, since the diagnosis content desired by the user is collected in the displacement-corrected boundary line information, a minimum requisite diagnosis time is necessary, whereby the efficiency of the diagnosis is improved. For this reason, a dynamic-state diagnosis can be executed appropriately and efficiently.

According to the image processing device of claim 2, the removal-required component includes at least one component among deformation components according to a vertical motion, a parallel motion, and rotation in the target area. Accordingly, the displacement-corrected boundary lines acquired by removing the deformations due to the vertical motion, the parallel motion, and the rotation from the target area boundary lines can be displayed.

According to the image processing device of claim 3, the frame selecting means is further included which executes, for selection target frame images including at least a plurality of frame images, the frame selecting process including the process of selecting the base frame image used for extracting the base boundary lines and reference frame images used for extracting the target area boundary lines other than the base boundary line, and the displacement calculating process includes the process of calculating a displacement amount between corresponding pixels of the target area boundary line of the base frame image as the base boundary line and the target area boundary lines of the reference frame image. Accordingly, frame images corresponding to user's diagnosis purpose can be selected, and the displacement-corrected boundary line information corresponding to the diagnosis purpose can be displayed. In addition, by selecting only necessary frame images, compared to the case where the displacement-corrected boundary lines are acquired for all the frame images included in the dynamic image, a calculation time required for the boundary line extracting process, the displacement amount calculating process, and the correction process can be minimized.

According to the image processing device of claim 4, the selection target frame images include frame images photographed in the past in time with respect to the plurality of frame images, and the frame selecting process includes a process of selecting a frame image photographed for the same body in the past in time with respect to the plurality of frame images as the base frame image. In other words, in a case where the present displacement-corrected boundary line information indicating the present displacement-corrected boundary lines is acquired, the base frame image can be executed by using a common (same) frame image photographed in the past. Accordingly, through a dynamic-state diagnosis, a comparison between the past and the present in the diaphragm boundary line LI of one body and a comparison between changes thereof can be made with high accuracy. For this reason, a follow-up observation can be accurately executed.

According to the image processing device of claim 5, the base frame image and the reference frame image are frame images when the target area periods are within a same period, and the frame selecting process includes a first selection process selecting one frame image as the base frame image from among (b1) to (b3) and a second selection process selecting one frame image as the reference frame image from among: (c1) to (c4). Accordingly, between frame images within the same period desired by the user, a change of the shape of the target area boundary line can be diagnosed with high precision.

According to the image processing device of claim 6, the target area boundary lines other than one of the target area boundary lines can be corrected with high accuracy by using the displacement amount between corresponding pixels of the base boundary line and one target area boundary line.

According to the image processing device of claim 7, the displacement amount used for the correction process is a displacement amount from the target area boundary line nearest in time from the target area boundary line that is a correction target. In other words, the reference frame image is changed for each calculation of the displacement amount, and the base frame image can be also changed. In this way, the base frame image can be changed in accordance with the change of the reference frame image.

Thus, by executing the correction process constantly using the displacement amount between diaphragm boundary lines of the selection target frame images that are nearest, the displacement-corrected boundary lines having higher correction accuracy can be acquired. As a result, the displacement-corrected boundary line information that is suitable for the diagnosis purpose can be displayed, and accordingly, the dynamic-state diagnosis can be executed more appropriately and efficiently.

According to the image processing device of claim 8, the displacement amount used for the correction process is a displacement amount between the base line boundary line and the target area boundary line, which is the correction target, that is acquired as a sum of displacement amounts of two boundary lines adjacent in time. In this way, in the displacement amount calculating process, one displacement amount between the base boundary line and the diaphragm boundary line is subdivided and calculated, and accordingly, compared to the displacement amount calculated without subdividing the base frame image to the reference frame image, the displacement amount can be calculated with high accuracy.

According to the image processing device of claim 9, a predetermined number of separate images separated for each predetermined number of displacement-corrected boundary lines are generated, and the predetermined number of separate images are sequentially displayed as displacement-corrected boundary line information. Thus, a change of the shape of the target area boundary line can be perceived based on the dynamic image.

According to the image processing device of claim 10, one still image is generated such that a predetermined number of displacement-corrected boundary lines are displayed in an overlapping manner, and the still image is displayed as the displacement-corrected boundary line information. For example, in a case where the shape of the predetermined number of the displacement-corrected boundary lines, which is a diagnosis target, is set as the displacement-corrected boundary line information, the displacement-corrected boundary lines can be displayed to be identifiable in an overlapping manner. Accordingly, a change of the shape of the target area boundary line can be perceived on one still image.

According to the image processing device of claim 11, the target area includes at least one of a diaphragm area and a heart area. Accordingly, diseases such as pulmonary emphysema and diaphragmatic eventration can be appropriately diagnosed through a dynamic-state diagnosis. In such a disease, in the case of a minor symptom, while the abnormality may not be noticed, by making a diagnosis using the displacement-corrected boundary line information, the diagnosis does not depend on the user's subjectivity, whereby an erroneous diagnosis can be prevented.

According to the image processing device of claim 12, the same effects as those of the inventions of claims 1 to 11 can be acquired.

Objects, features, aspects, and advantages of the present invention will become more apparent by detailed description presented below and the attached drawings.

BRIEF DESCRIPTION OF DRAWINGS

FIG. 2 is a diagram that illustrates a relation between a respiratory motion and the position of the diaphragm.

FIG. 30 is a schematic view of a heartbeat phase representing the motion of a heart wall in a time series.

DESCRIPTION OF EMBODIMENTS

1. First Embodiment

Hereinafter, a radiation dynamic image photographing system according to a first embodiment of the present invention will be described.

<1-1. Whole Configuration of Radiation Dynamic Image Photographing System>

The radiation dynamic image photographing system according to the first embodiment photographs a radiation image for a situation in which the physical state of a target area of a subject periodically changes in time by using a human body or an animal body as the subject.

Figure 1:
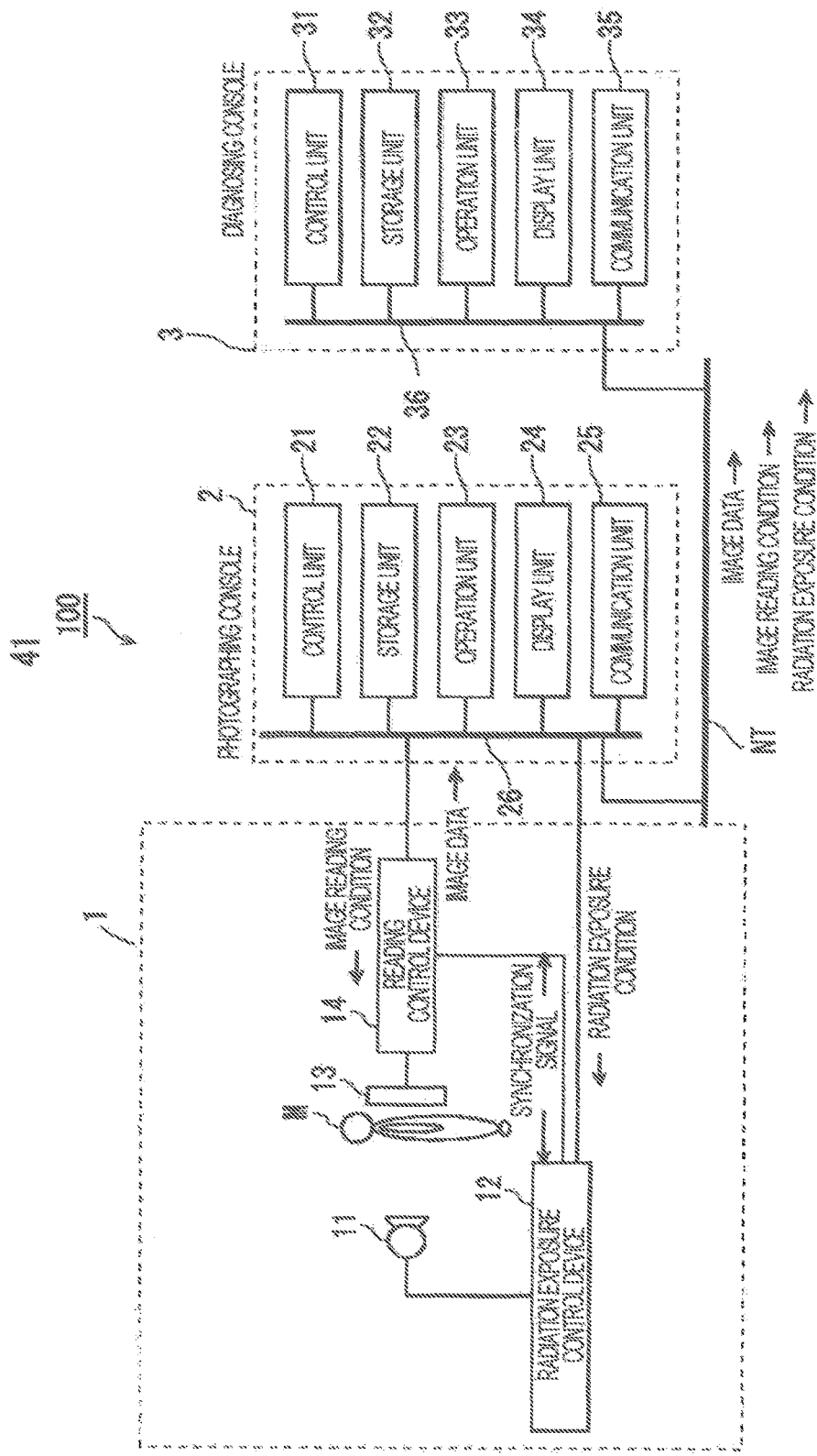
FIG. 1 is a diagram that illustrates the whole configuration of a radiation dynamic image photographing system 100 according to a first embodiment.

FIG. 1 is a diagram that illustrates the whole configuration of the radiation dynamic image photographing system 100 according to the first embodiment. As illustrated in FIG. 1, the radiation dynamic image photographing system 100 includes: a photographing apparatus 1; a photographing control device 2 (photographing console); and an image processing device 3 (diagnosing console). The photographing apparatus 1 and the photographing control device 2 are interconnected through a communication cable or the like, and the photographing control device 2 and the image processing device 3 are configured to be interconnected through a communication network NT such as a local area network (LAN). Each device configuring the radiation dynamic image photographing system 100 is compliant with the digital image and communications in medicine (DICOM) standard, and communication between the devices is executed in compliance with the DICOM standard.

<1-1-1. Configuration of Photographing Apparatus 1>

The photographing apparatus 1, for example, is an apparatus that is configured by an X-ray photographing apparatus or the like and photographs the dynamic state of the chest of a subject M according to respiration. The photographing of a dynamic state is executed by acquiring a plurality of images in order of time while repeatedly emitting a radiation ray such as an X ray to the chest of the subject M. A series of images acquired by such continuous photographing are called a dynamic image. In addition, each of a plurality of images configuring the dynamic image is called a frame image.

As illustrated in FIG. 1, the photographing apparatus 1 is configured to include: a radiation unit (radiation ray source) 11; a radiation exposure control device 12; an imaging unit (radiation detecting unit) 13, and a reading control device 14.

The radiation unit 11 emits a radiation ray (X ray) to the subject M in accordance with control of the radiation exposure control device 12. An example illustrated in the figure is a system for a human body, and the subject M corresponds to an inspection target person. Hereinafter, the subject M may be also referred to as an "examinee".

The radiation exposure control device 12 is connected to the photographing control device 2 and executes radiation photographing by controlling the radiation unit 11 based on a radiation exposure condition input from the photographing control device 2.

The imaging unit 13 is configured by a semiconductor image sensor such as an FPD and converts a radiation ray that is emitted from the radiation unit 11 and is transmitted through the examinee M into an electrical signal (image information).

The reading control device 14 is connected to the photographing control device 2. The reading control device 14 acquires image data by switching the reading of an electrical signal stored in each pixel and reading the electrical signal stored in the imaging unit 13 by controlling the switching unit of each pixel of the imaging unit 13 based on an image reading condition input from the photographing control device 2. Then, the reading control device 14 outputs the acquired image data (frame image) to the photographing control device 2. The image reading condition, for example, is a frame rate, a frame interval, a pixel size, an image size (matrix size), or the like. The frame rate is the number of frame images acquired per second and matches a pulse rate. The frame interval is a time from the start of operation of acquiring a frame image of one time to the start of operation of acquiring a next frame image in continuous photographing and matches a pulse interval.

Here, the radiation exposure control device 12 and the reading control device 14 are interconnected, exchange a synchronization signal, and are configured to synchronize a radiation exposure operation and an image reading operation with each other.

<1-1-2. Configuration of Photographing Control Device 2>

The photographing control device 2 controls the radiation photographing operation and the operation of reading a radiation image executed by the photographing apparatus 1 by outputting a radiation control condition and an image reading condition to the photographing apparatus 1 and displays a dynamic image acquired by the photographing apparatus 1 for checking whether it is an image appropriate for checking or diagnosing positioning executed by a cameraman.

As illustrated in FIG. 1, the photographing control device 2 is configured to include a control unit 21, a storage unit 22, an operation unit 23, a display unit 24, and a communication unit 25, and such units are interconnected through a bus 26.

The control unit 21 is configured by a central processing unit (CPU), random access memory (RAM), and the like. The CPU of the control unit 21 reads a system program or various processing programs stored in the storage unit 22 and expands the program within the RAM in accordance with operation using the operation unit 23, executes various operation starting from a photographing control process to be described later according to the expanded program, thereby controlling the operation of each unit of the photographing control device 2 and the operation of the photographing apparatus 1 in a centralized manner.

The storage unit 22 is configured by nonvolatile semiconductor memory, a hard disk, or the like. The storage unit 22 stores various programs executed by the control unit 21, parameters necessary for the execution of the process for the programs, or data such as a processing result.

The operation unit 23 is configured by a keyboard including a cursor key, numeric input keys, various functional keys, and the like and a pointing device such as a mouse and outputs an instruction signal input through a key operation for the keyboard, a mouse operation, or a touch panel to the control unit 21.

The display unit 24 is configured by a monitor such as a color liquid crystal display (LCD) and displays an input instruction supplied from the operation unit 23, data, or the like in accordance with an instruction for a display signal input from the control unit 21.

The communication unit 25 includes a LAN adapter, a modem, a terminal adapter (TA) or the like and controls transmission/reception of data to/from each device connected to the communication network NT.

<1-1-3. Configuration of Image Processing Device 3>

The image processing device 3 acquires a dynamic image transmitted from the photographing apparatus 1 through the photographing control device 2 and displays an image used for radiogram interpretation to be made by a doctor or the like.

As illustrated in FIG. 1, the image processing device 3 is configured to include a control unit 31, a storage unit 32, an operation unit 33, a display unit 34, a communication unit 35, and an analysis unit 36, and such units are interconnected through a bus 37.

The control unit 31 is configured by a CPU, RAM, and the like. The CPU of the control unit 31 reads a system program or various processing programs stored in the storage unit 32 in accordance with operation using the operation unit 33, expands the program into the RAM, and executes various processes according to the expanded program, thereby controlling the operation of each unit of the image processing device 3 in a centralized manner (detailed description will be presented later).

The storage unit 32 is configured by nonvolatile semiconductor memory, a hard disk, or the like. The storage unit 32 stores various programs executed by the control unit 31, parameters necessary for the execution of the process for the programs, or data such as a processing result. For example, the storage unit 32 stores an image processing program used for executing image processing to be described later. Such various programs are stored in the form of a readable program code, and the control unit 31 sequentially executes operation according to the program code.

The operation unit 33 is configured by a keyboard including a cursor key, numeric input keys, various functional keys, and the like and a pointing device such as a mouse and outputs an instruction signal input through a key operation for the keyboard, a mouse operation, or a touch panel to the control unit 31.

The display unit 34 is configured by a monitor such as a color LCD and displays an input instruction supplied from the operation unit 33, data, and a display image to be described later in accordance with an instruction for a display signal input from the control unit 31.

The communication unit 35 includes a LAN adapter, a modem, a TA or the like and controls transmission/reception of data to/from each device connected to the communication network NT.

<1-2. Relation Between Respiratory Motion and Position of Diaphragm and Problem in Diagnosis of Dynamic State>

As a premise for detailed description of the image processing device 3 according to this embodiment, a relation between a respiratory motion and the position of the diaphragm and problems in the diagnosis of a dynamic state according thereto will be described.

FIG. 2 is a diagram that illustrates a general relation between a respiratory motion and the position of the diaphragm. FIG. 2A is a schematic view of the side face of the inside of a human body at the time of breathing in (at the time of inhalation), FIG. 2B is a schematic view of the side face of the inside of the human body at the time of breathing out (at the time of exhalation), and FIG. 2C is a schematic view that represents situations on the side face of the inside of the human body both at the time of exhalation and at the time of inhalation altogether.

As illustrated in FIG. 2C when left and right thoracic cavities 52 that are sealed by being enclosed by the thorax 53 and the diaphragm 50 inflate, the air is inhaled, and, when the left and right thoracic cavities 52 contract, the air is exhaled, whereby respiration is made. In other words, as illustrated in FIG. 2A, at the time of inhalation, the diaphragm 50-1 is lowered as denoted by arrow AR11, and a rib is lifted as denoted by arrow AR12. Accordingly, the thoracic cavities 52 expand, and the air is inhaled into the lung through a trachea 51 as denoted by arrow AR13. On the other hand, as illustrated in FIG. 2B, at the time of exhalation, the diaphragm 50-2 is lifted as denoted by arrow AR21, and the rib is lowered as denoted by arrow AR22. Accordingly, the thoracic cavities 52 are narrowed, and the air is exhaled from the lung through the trachea 51 as denoted by arrow AR23. Such a motion of the diaphragm 50 takes charge of about 60% of the respiratory motion.

In the example illustrated in FIG. 2 described above, while the relation between the respiratory motion of a healthy person and the position of the diaphragm 50 has been described, for example, for an unhealthy person who has suffered from illness such as pulmonary emphysema, a bronchus becomes thin due to a damage of pulmonary alveoli, and, even when a breath is given out, the air does not come out from the lung, the lung excessively expands, and a state is maintained in which the lung presses down the diaphragm 50 in the state in which a breath is given out. In other words, the diaphragm 50 is not moved, and the respiratory motion cannot be made well.

In addition, for an unhealthy person who has suffered from illness of the diaphragm such as diaphragmatic eventration, in a state in which one side or both sides of the diaphragm 50 are not moved, a phrenic nerve moving the diaphragm 50 is disordered caused by mediastinum, tumors of the lung, an aortic aneurysm, an external wound, operation of the mediastinum, or the like, whereby paralysis of the diaphragm occurs.

In making a dynamic-state diagnosis for an unhealthy person who has suffered from such illness, when an inspection is made by using a chest X-ray dynamic image, a state is formed in which the diaphragm 50 does not move even when respiration is made with being pressed down or raised up.

While it is possible even for a user such as an experienced doctor to easily make a diagnosis in a case where the illness is serious, in the case of minor illness, the diagnosis depends on user's subjectivity, ambiguity may remain, which may lead to making a wrong diagnosis.

In addition, in order to prevent the wrong diagnosis described above, the user needs to make a dynamic-state diagnosis by making a detailed observation or making an observation of a difference from the motion according to a healthy person's respiration. Thus, a lot of observation time is consumed, whereby the diagnosis efficiency is very low.

Furthermore, since the diaphragm has a cubic shape, it is difficult to perceive the motion of the diaphragm by perceiving the shape of the diaphragm based on an X-ray dynamic image that has been actually photographed. In addition, it is necessary to make a diagnosis based on the shape of left and right pulmonary fields and a change in the motion. However, for a user who has insufficient experiences of diagnoses according to a dynamic-state diagnosis, it is difficult to perceive and determine an abnormal shape change in the left and right pulmonary fields based on a dynamic image in which a plurality of motions such as a positional variation and a shape variation are caused even in a normal respiration operation.

Under such a background, it is desirable to display analysis information that is effective for a diagnosis without depending on the user's subjectivity.

Thus, in the present invention, by displaying boundary line information acquired by removing unnecessary deformations between frame images from the boundary line of a target area, it is possible to perceive the motion of the shape of a target area.

Hereinafter, the image processing device 3 according to the first embodiment will be described in detail.

<1-3. Specific Configuration of Image Processing Device 3>

The image processing device 3 of the radiation dynamic image photographing system 100 according to the first embodiment of the present invention displays boundary line information acquired by removing deformations according to a vertical motion, a parallel motion, and rotation between frame images, whereby a dynamic-state diagnosis can be made appropriately and efficiently.

Hereinafter, the functional configuration realized by the image processing device 3 will be described.

<1-3-1. Functional Configuration of Image Processing Device 3>

Figure 3:
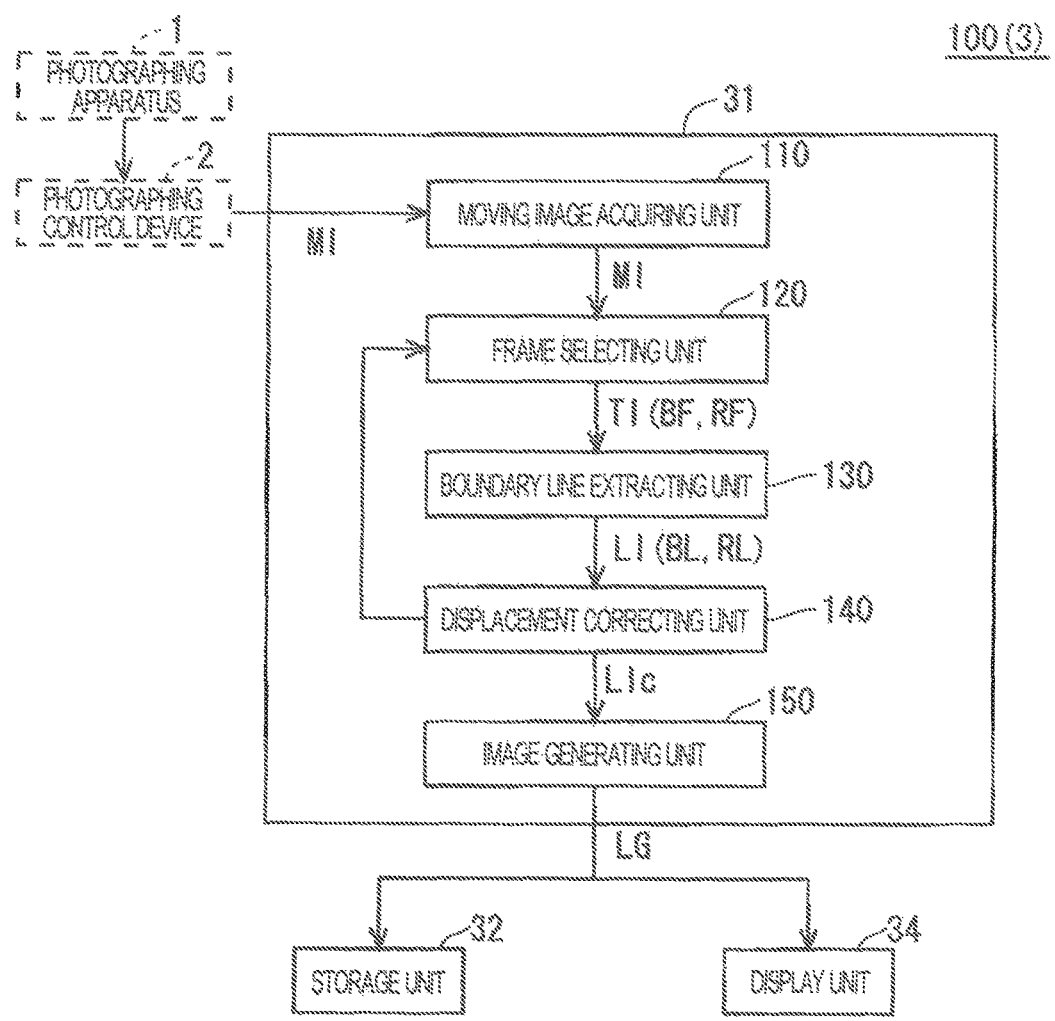
FIG. 3 is a block diagram that illustrates the functional configuration of an image processing device 3 according to the first embodiment.

FIG. 3 is a diagram that illustrates the functional configuration realized by the control unit 31 by operating the CPU and the like according to various programs in the image processing device 3 of the radiation dynamic image photographing system 100 together with other configurations. The image processing device 3 according to this embodiment uses a dynamic image acquired by photographing the chest mainly including the heart and both lungs.

The control unit 31 is mainly configured by: a dynamic-image acquiring unit 110; a frame selecting unit 120; a boundary line extracting unit 130; a displacement correcting unit 140; and an image generating unit 150.

Hereinafter, while the functional configuration of the control unit 31 as illustrated in FIG. 3 will be described to be realized by executing a program that has been installed in advance, the functional configuration may be realized by a dedicated hardware configuration.

Hereinafter, specific contents of the processes executed by the dynamic image acquiring unit 110, the frame selecting unit 120, the boundary line extracting unit 130, the displacement correcting unit 140, and the image generating unit 150 will be sequentially described with reference to FIG. 3.

<1-3-1-1. Dynamic Image Acquiring Unit 110>

The dynamic image acquiring unit 110 acquires a dynamic image configured by a plurality of frame images acquired by sequentially photographing in the time direction changing states of the physical state of a target area with respect to time inside the body of an examinee M that are photographed by the reading control device 14 of the photographing apparatus 1. The target area according to this embodiment is assumed to be a diaphragm area. In other words, as illustrated in FIG. 3, the photographing control device 2 is interposed between the photographing apparatus 1 and the image processing device 3, and detection data (a plurality of frame images MI) stored in the storage unit 22 of the photographing control device 2 is output to the communication unit 35 of the image processing device 3 through the communication unit 25.

Figure 4:
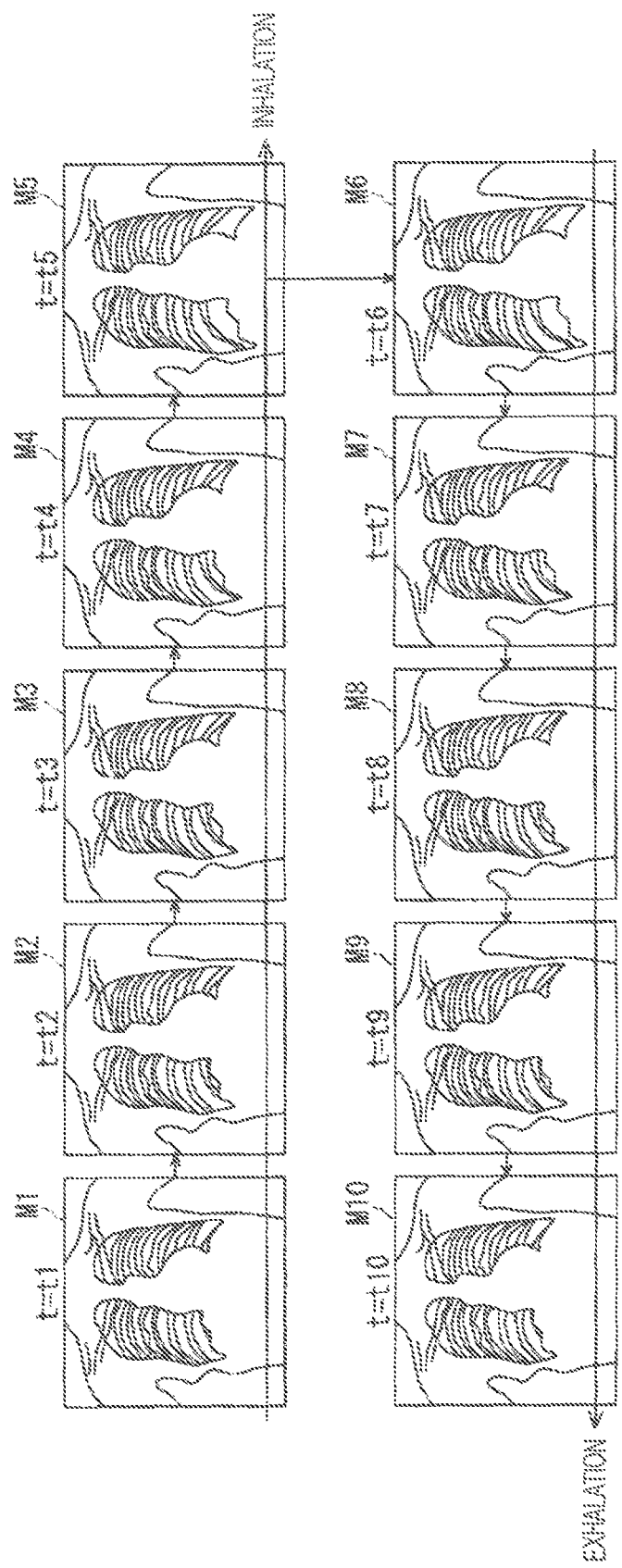
FIG. 4 is a diagram that illustrates a dynamic image acquired through radiation dynamic image photographing as an example.

FIG. 4 is a diagram that illustrates a dynamic image acquired through radiation dynamic image photographing of dynamic states of the chest of the examinee M accompanied with respiration as an example. As illustrated in FIG. 4, frame images M1 to M10 (MI) acquired by the dynamic image acquiring unit 110 are acquired by continuously photographing for one period of the respiratory cycle at predetermined photographing timings. More specifically, images acquired at the photographing timings of time t=t1, t2, t3, . . . , t10 respectively correspond to frame images M1, M2, M3, . . . , M10.

<1-3-1-2. Frame Selecting Unit 120>

The frame selecting unit 120 executes a frame selecting process including the process of selecting a base frame image BF used for extracting a base boundary line BL to be described later and a reference frame image RF used for extracting diaphragm boundary lines LI (to be described later in detail) other than the base boundary line BL for selection target frame images TI including at least a first number of (a plurality of) frame images MI that is at least two or more.

Figure 5:
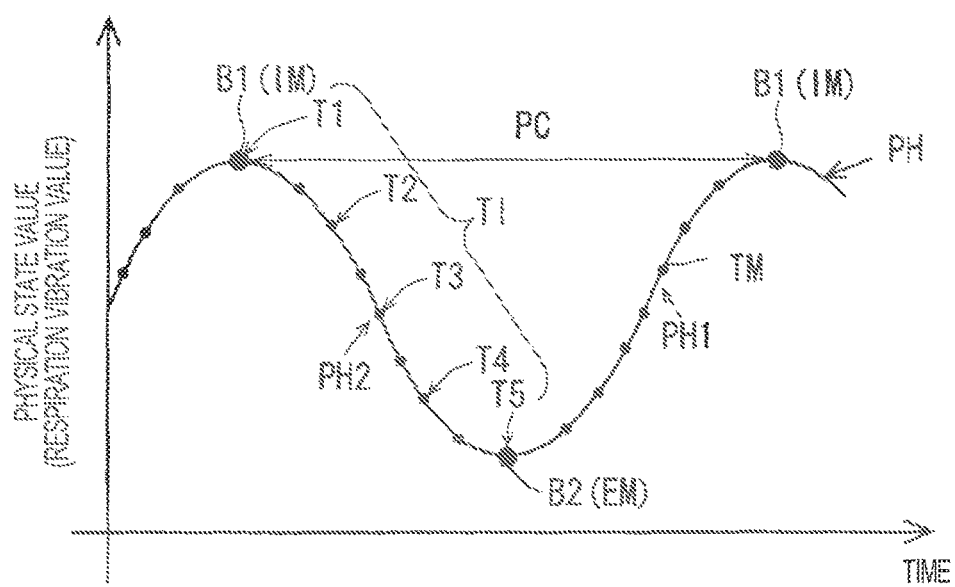
FIG. 5 is a schematic view that illustrates a respiration phase representing waveform data of a respiration vibration value in a time series and photographing timings altogether.

FIG. 5 is a schematic view that illustrates a respiration phase PH representing waveform data of a (physical state value (respiration vibration value) to be described later in a time series and photographing timings TM altogether and is a diagram that illustrates the frame selecting process. As illustrated in FIG. 5, for example, in a case where the selection target frame images TI are assumed to be T1 to T5, in the frame selecting process, the base frame image BF and the reference frame image RF are selected from among the frame images T1 to T5 (TI).

<1-3-1-3. Boundary Line Extracting Unit 130>

The boundary line extracting unit 130 executes a boundary line extracting process in which a first number of (a plurality of) target area boundary lines are acquired by extracting boundary lines of a target area from the selection target frame image TI. Since the target area according to this embodiment is the diaphragm area, hereinafter, the target area boundary lines will be described as diaphragm boundary lines.

The boundary line extracting unit 130 executes the boundary line extracting process for the base frame image BF and the reference frame image RF selected by the frame selecting unit 120. In other words, the diaphragm boundary line LI for the base frame image BF corresponds to the base boundary line BL, and the diaphragm boundary line LI for the reference frame image RF corresponds to the reference boundary line RL. Then, the boundary line extracting unit 130 outputs the base boundary line BL and the reference boundary line RL to the displacement correcting unit 140 (see FIG. 3).

Figure 6:
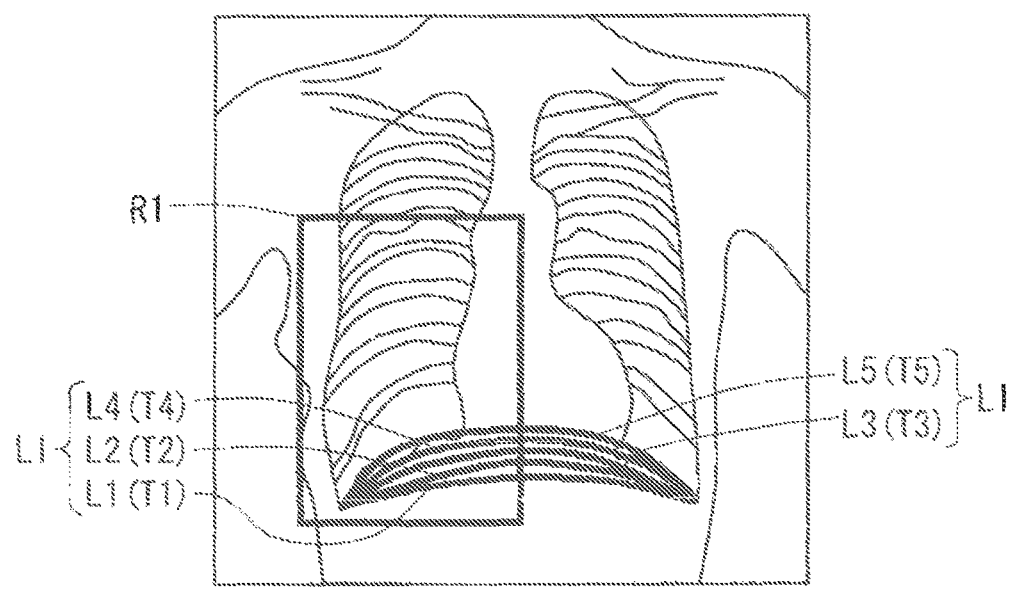
FIG. 6 is a schematic view that illustrates a diaphragm boundary line at an exhalation phase.
Figure 7:
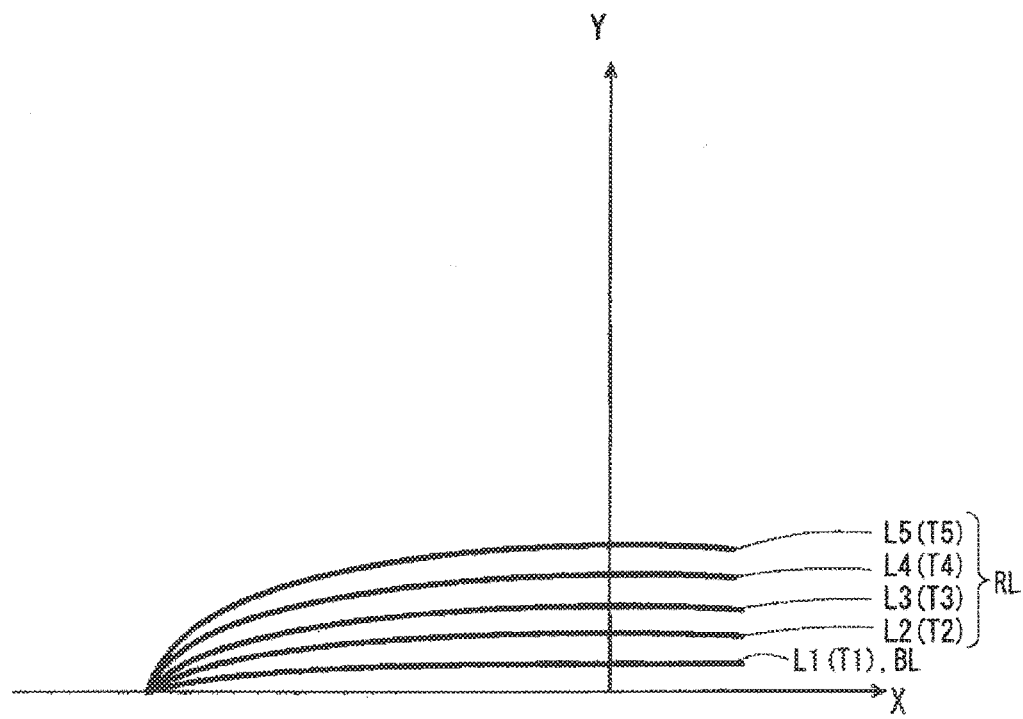
FIG. 7 is a schematic view that illustrates a diaphragm boundary line at the time of an exhalation phase as an example with coordinates being assigned thereto.

FIGS. 6 and 7 are schematic views that illustrate diaphragm boundary lines at the time of an exhalation phase PH2 (see FIG. 5). FIG. 7 is a schematic view that illustrates the diaphragm boundary lines in an orthogonal coordinate system at the time of the exhalation phase PH2 in an area R1 illustrated in FIG. 6.

As illustrated in FIGS. 6 and 7, diaphragm boundary lines L1 to L5 (LI) are respectively extracted from the selection target frame images T1 to T5 (TI) illustrated in FIG. 5 described above that correspond to the base frame image BF and the reference frame image RF.

Hereinafter, while a method of extracting diaphragm boundary lines will be described more specifically, the extraction method is not limited to the method described here, but any method capable of extracting diaphragm boundary lines from a dynamic image may be used.

<1-3-1-3-1. First Boundary Line Extracting Process>

Figure 8A:
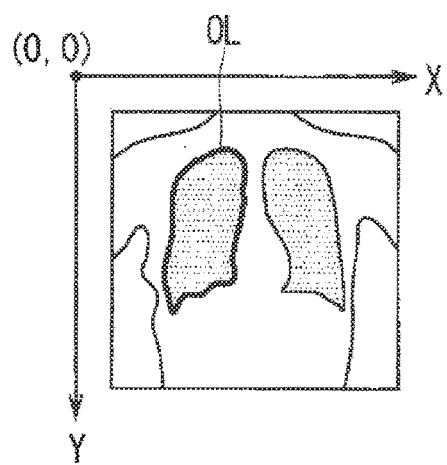
FIG. 8 is a schematic view that illustrates extraction of the contour of a pulmonary field area including a diaphragm boundary line as an example.
Figure 8B:
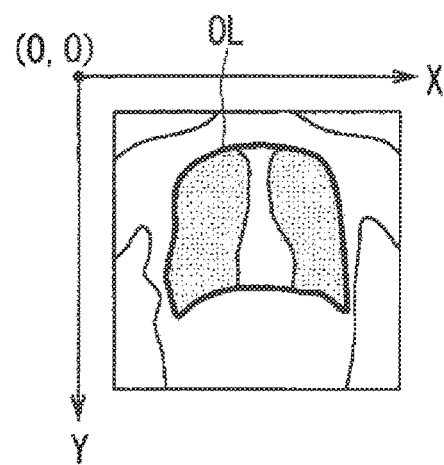

A first boundary line extracting process is a process of extracting a diaphragm boundary line LI by executing contour extraction of a pulmonary field part based on the selection target frame image TI. FIG. 8 is a schematic view that illustrates contour extraction of a pulmonary field part including the diaphragm boundary line LI. The pulmonary field part, as illustrated in FIG. 8, may be extracted for each of the left and right sides (see FIG. FIG. 8a) or may be extracted as a contour (see FIG. 8B) including the areas of the heart and the spine. As this extraction method, a conventional technology (for example, see "Image feature analysis and computer-aided diagnosis: Accurate determination of ribcage boundary in chest radiographs", Xin-Wei Xu and Kunio Doi, Medical Physics, Volume 22(5), May 1995, pp. 617-626)) or the like may be employed.

<1-3-1-3-2. Second Boundary Line Extracting Process>

A second boundary line extracting process is a process of extracting the diaphragm boundary line LI through model-based extraction. In other words, candidate positions of the diaphragm are roughly extracted through template matching that is one of model-based techniques (rough extraction), and the extracted candidate areas are analyzed in detail (fine extraction), whereby the diaphragm boundary line is extracted with high accuracy. For the rough extraction at this time, by using medical knowledge relating to the motion of the diaphragm, templates can be weighted according to the amount of motion of the diaphragm, and the accuracy of the rough extraction can be improved, whereby the extraction accuracy of the diaphragm boundary line LI can be improved. As this extraction method, for example, "Patent Application OPI No. 2012-138364 (Application Date: Jun. 20, 2012)" that is an application filed by the present applicant may be employed.

<1-3-1-3-3. Third Boundary Extracting Process>

Figure 9A:
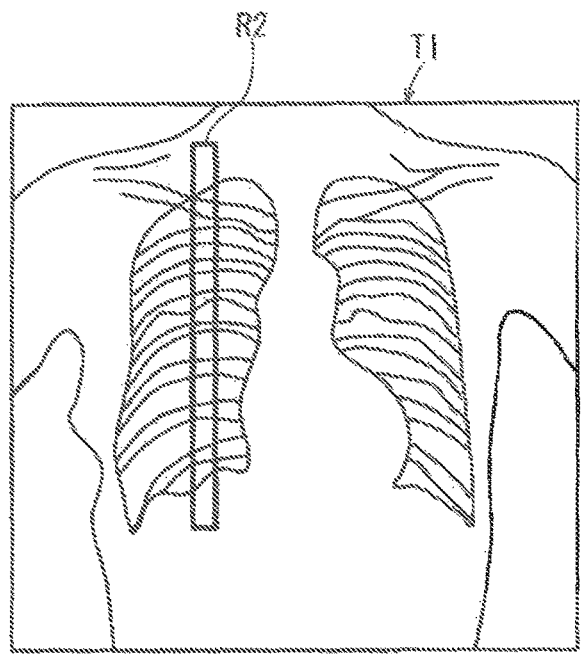
FIG. 9 is a schematic view that illustrates extraction of the contour of the pulmonary field area including the diaphragm boundary line as an example.
Figure 9B:
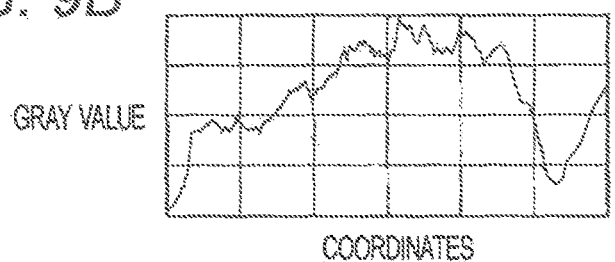

A third boundary line extracting process is a process of extracting the diaphragm boundary line LI through extraction according to a profile analysis. FIG. 9 is a diagram that illustrates the profile analysis. FIG. 9A is a diagram that illustrates a profile area R2 of the selection target frame image TI, and FIG. 9B is a graph of which the vertical axis represents a gray value for vertical coordinates the profile area R2 (see FIG. 9A) of the selection target frame image TI of the horizontal axis. As illustrated in FIG. 9, the profile R2 is generated in the vertical direction, and points at which the peak of the gray value changes in the generated profile R2 can be extracted as a boundary line of the diaphragm.

<1-3-1-3-4. Fourth Boundary Extracting Process>

A fourth boundary line extracting process is a process of extracting the diaphragm boundary line LI through extraction according to a user's designation. More specifically, the user designation may be made by simply allowing a user to draw a line of the extraction target of the diaphragm boundary line LI or may be used as a method for correcting the diaphragm boundary line LI extracted by the first to third boundary line extracting processes. In addition, in the former case where the line is simply designated by the user, it is preferable that only one of the selection target frame images TI that are targets is designated by the user, and the remaining frame images are traced by employing a corresponding point search method in the time direction or the like.

<1-3-1-4. Displacement Correcting Unit 140>

Figures 10A, 10B, 10C:
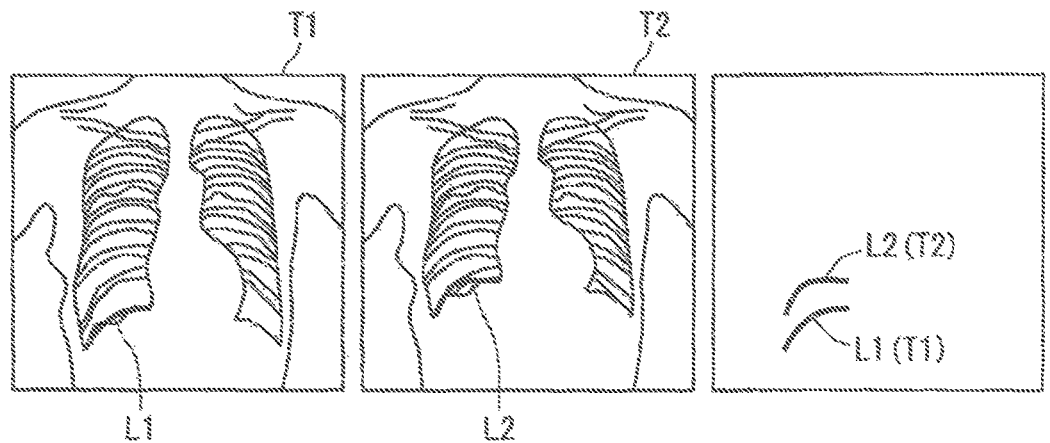
FIG. 10 is a schematic view that illustrates a displacement amount between diaphragm boundary lines.

FIG. 10 is a schematic view that illustrates a displacement amount between diaphragm boundary lines LI in the selection target frame image TI extracted by the boundary line extracting unit 130. FIGS. 10A and 10B illustrate diaphragm boundary lines L1 and L2 in frame images T1 and T2 extracted by the boundary line extracting unit 130, and FIG. 10C displays the diaphragm boundary lines L1 and L2 in an overlapping manner.

Figure 11A:
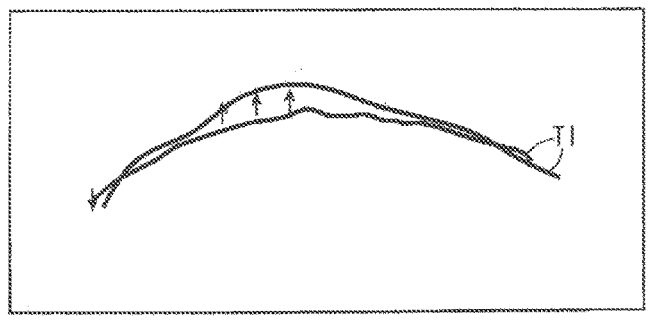
FIG. 11 is a schematic diaphragm that illustrates a displacement amount between diaphragm boundary lines.
Figure 11B:
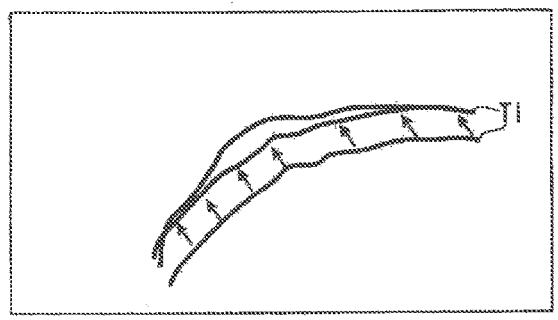

FIG. 11 is a schematic view that illustrates two examples of the displacement amount between the diaphragm boundary lines LI in the selection target frame image TI extracted by the boundary line extracting unit 130. FIG. 11A illustrates a deformation according to a vertical motion as an example, and FIG. 11B illustrates deformations according to a parallel motion and rotation as an example.

In other words, in changes of the shape of the diaphragm boundary line LI between the selection target frame images TI extracted by the boundary line extracting unit 130 as illustrated in FIG. 11, two kinds of changes including (i) a motion in which the shape of the diaphragm boundary line LI changes, in other words, a "shape deformation" and (ii) a motion accompanying a respiration motion of the diaphragm, in other words, a "deformation according to a vertical motion, a parallel motion, and rotation" as illustrated in FIGS. 11A and 11B are included. Of the deformations, in order to acquire only the shape deformation of (i), it is necessary to remove the deformation (see FIG. 11) according to the vertical motion, the parallel motion, and the rotation of (ii) from the diaphragm boundary line LI.

Thus, the displacement correcting unit 140 executes the following two processes. As a first process, a displacement amount calculating process is executed in which, by using pixels corresponding to a first number (a plurality of) diaphragm boundary lines LI, a displacement amount D acquired by using the base boundary line BL as a displacement base is calculated for one or more diaphragm boundary lines LI other than the base boundary line BL among the predetermined first number of diaphragm boundary lines LI. Here, the displacement amount D represents a removal-required component, and the removal-required component includes at least one component of deformation components according to a vertical motion, a parallel motion, and rotation in the diaphragm area.

Next, as a second process, a correction process is executed in which, after the displacement amount calculating process, a second number (a predetermined number acquired by excluding the base boundary line BL), which is the first number or less, of the diaphragm boundary lines LI are corrected by using the displacement amount D. By executing such two processes, the second number (predetermined number) of displacement-corrected boundary lines LIc from which the removal-required component has been removed are acquired (see FIG. 3).

In other words, the displacement correcting unit 140 receives the base boundary line BL and the reference boundary line RL extracted by the boundary line extracting unit 130 and executes the displacement amount calculating process and the correction process. Here, in the displacement amount calculating process, a displacement amount between pixels corresponding to the base boundary line BL and the reference boundary line RL is calculated. Then, in the correction process, a correction process is executed for the diaphragm boundary line LI that is the correction target by using the displacement amount, whereby a displacement-corrected boundary line LIc is acquired. Here, the diaphragm boundary line LI that is the correction target corresponds to the reference boundary line RL.

Figure 12:
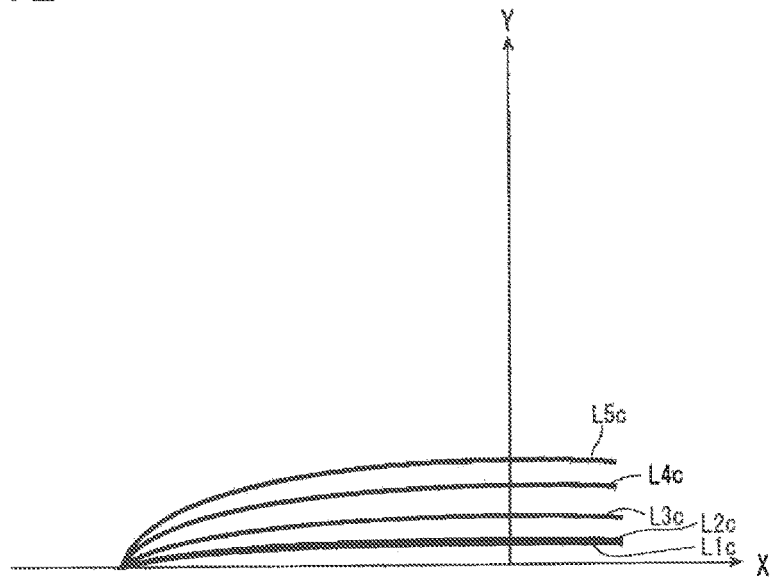
FIG. 12 is a schematic view that illustrates displacement-corrected boundary lines at the time of an exhalation phase as an example.

FIG. 12 is a schematic view that illustrates a displacement-corrected boundary line LIc at the time of the exhalation phase PH2 (see FIG. 5). The displacement-corrected boundary lines L1c to L5c (LIc) illustrated in FIG. 12 correspond to boundary lines acquired by removing the removal-required components from the diaphragm boundary lines L1 to L5 (LI) (in other words, the diaphragm boundary line LI that is the correction target) illustrated in FIGS. 6 and 7 by using the displacement correcting unit 140. Here, in the example illustrated in FIG. 12, since the base boundary line BL is set as the diaphragm boundary line L1, the frame selecting unit 120 selects the base frame image BF as the frame image T1 and selects the reference frame images RF (frame images that are correction targets) as the frame images T1 to T5. In other words, the displacement correcting unit 140 executes the correction process with the base boundary line BL set as the diaphragm boundary line L1 and the reference boundary line RL being set as the diaphragm boundary lines L1 to L5, thereby acquiring displacement-corrected boundary lines L1c to L5c (LIc).

Hereinafter, after four methods will be specifically described for the displacement amount calculating process, two methods will be specifically described for the correction process. This embodiment is not limited to those methods, but any other method may be used as long as the displacement amount calculating process and the correction process can be appropriately executed.

<1-3-1-4-1. First Displacement Amount Calculating Process>

A first displacement amount calculating process is effective only in a case where the deformation of (ii) described above is due to only the vertical motion. In other words, the process is executed under the premise that the displacement amount between the diaphragm boundary lines LI is only in the vertical direction.

Figure 13:
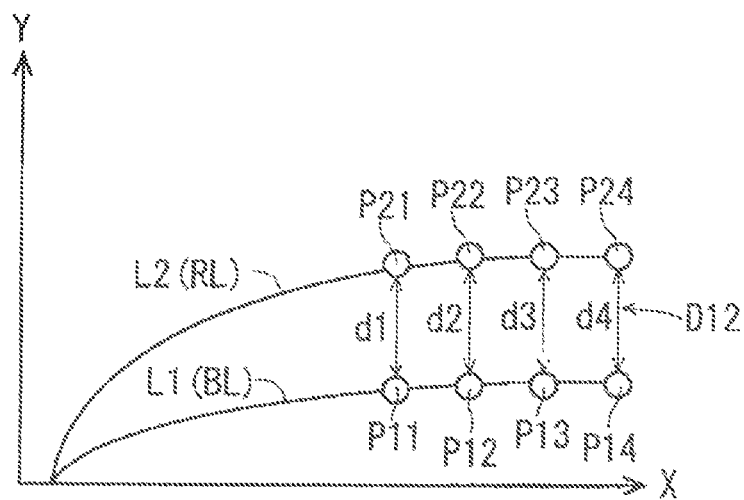
FIG. 13 is a schematic view that illustrates a displacement amount calculating process.

FIG. 13 is a schematic view that illustrates a first displacement amount calculating process. As illustrated in FIG. 13, a case will be considered in which the base boundary line BL is set as the diaphragm boundary line L1, the reference boundary line RL is set as the diaphragm boundary line L2, and pixels of the diaphragm boundary line L2 that correspond to pixels P11, P12, P13, and P14 of the diaphragm boundary line L1 are pixels P21, P22, P23, and P24. Here, for the convenience of description, while only four corresponding pixels are representatively illustrated for each of the base boundary line BL and the reference boundary line RL, actually, corresponding pixels of the base boundary line BL and the reference boundary line RL are appropriately designated.

At this time, a displacement amount of the diaphragm boundary line L2 with respect to the diaphragm boundary line L1, in other words, a displacement amount of a corresponding pixel is only in the Y-axis direction. In other words, a "displacement amount d1 between the pixels P11 and P21", a "displacement amount d2 between the pixels P12 and P22", a "displacement amount d3 between the pixels P13 and P23", and a "displacement amount d4 between the pixels P14 and P24" calculated in the first displacement amount calculating process are only Y-component values.

For example, instead of using the values of the displacement amounts d1 to d4 as the displacement amount D12 between the base boundary line BL and the reference boundary line RL, an average value, a minimal value, or a maximum value of the displacement amounts d1 to d4 may be used as the displacement amount D12 between the base boundary line BL and the reference boundary line RL. This displacement amount D12 is a vertical motion deformation component between the base boundary line BL and the reference boundary line RL.

<1-3-1-4-2. Second Displacement Amount Calculating Process>

A second displacement amount calculating process is effective in a case where the deformation of (ii) described above is due to not only the vertical motion but also a parallel motion or rotation. In other words, the process is executed under the premise that the displacement amount between the diaphragm boundary lines LI includes all the vertical motion, the parallel motion, and the rotation.

Figure 14:
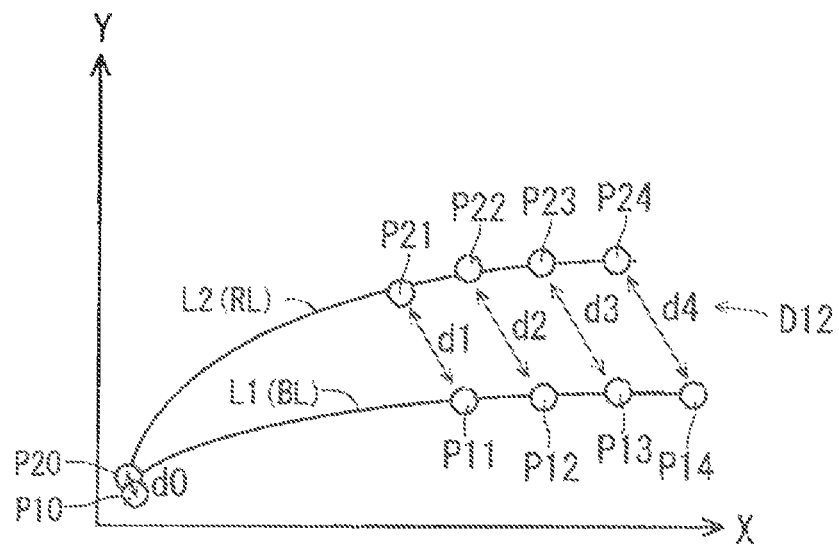
FIG. 14 is a schematic view that illustrates a displacement amount calculating process.

FIG. 14 is a schematic view that illustrates a second displacement amount calculating process. Reference signs used in FIG. 14 are common to those used in FIG. 13. A difference of the case illustrated in FIG. 14 from that illustrated in FIG. 13 is that a method of designating a corresponding pixel is different. In other words, in the second displacement amount calculating process, the displacement amount D12 is calculated such that endpoints match each other. More specifically, rotation and parallel movement are made such that the end points of the diaphragm boundary lines L1 and L2, in other words, the pixels P10 and P20 and the pixels P14 and P24 match each other, and displacement amounts d1 to d4 are calculated for coordinate points present between the end points.

For example, instead of using values of parallel motion amounts or rotation angles that can be calculated based on the displacement amounts d1 to d4 illustrated in FIG. 14 as the displacement amount D12 between the base boundary line BL and the reference boundary line RL, an average value (a minimal value or a maximum value) of the parallel motion amounts or the rotation angles or an amount requested for a combination thereof may be used as the displacement amount D12 between the base boundary line BL and the reference boundary line RL. This displacement amount D12 is a deformation component according to the parallel motion and the rotation between the base boundary line BL and the reference boundary line RL.

In addition, the displacement amounts d1 to d4 between pixels illustrated in FIG. 14 correspond to distances between points that are closest to each other. Here, when rotation or a parallel motion is made, an affine transformation or the like may be employed. In addition, by employing a least square method, distances between points that are closest to each other may be acquired.

<1-3-1-4-3. Third Displacement Amount Calculating Process>

A third displacement amount calculating process is effective in a case where the deformation of (ii) described above is due to not only the vertical motion but also a parallel motion or rotation. In other words, the process is executed under the premise that the displacement amount between the diaphragm boundary lines LI includes all the vertical motion, the parallel motion, and the rotation.

In the third displacement amount calculating process, a displacement amount D is calculated through shape fitting. As a specific method of fitting calculation, for example, an iterative closest point (ICP) algorithm or the like may be used. When the ICP algorithm is used, by parallel moving or rotating one boundary line of the base boundary line BL and the reference boundary line RL, convergence calculation can be executed such that a distance between corresponding pixels is minimal. Here, while the ICP algorithm has been described as an example, any other method executing fitting such that a distance between corresponding pixels is minimal through convergence calculation may be used. As an advantage of executing fitting through convergence calculation such as the ICP algorithm, more detailed shape matching can be made, and accordingly, an accurate displacement amount D can be calculated.

In this way, a displacement amount D between the base boundary line BL and the reference boundary line RL is acquired such that a distance between corresponding pixels is minimal through the fitting process. This displacement amount D is a deformation component according to the parallel motion and the rotation between the base boundary line BL and the reference boundary line RL.

<1-3-1-4-4. Fourth Displacement Amount Calculating Process>

A fourth displacement amount calculating process is effective in a case where the deformation of (ii) described above is due to not only the vertical motion but also a parallel motion or rotation. In other words, the process is executed under the premise that the displacement amount between the diaphragm boundary lines LI includes all the vertical motion, the parallel motion, and the rotation.

In the fourth displacement amount calculating process, each corresponding pixel of the reference boundary line RL for the base boundary line BL is tracked, and a "tracking result" is calculated as a displacement amount D. As a specific tracking calculation method, a method as described below may be employed.

For example, a POC (phase restricting correlation) may be employed. In the POC algorithm, a correlation (similarity) between a registration image (base boundary line BL) that becomes a background and an input image (reference boundary line RL) to be checked is calculated. More specifically, when an image formed as a digital signal is mathematically processed through a Fourier transform, the image is decomposed into an amplitude (gray data) and a phase (contour data of the image). Out of the two kinds of information, the amplitude information in which shape information is not included is not used, and image processing of the correlation can be instantly executed by using only the phase information. Accordingly, as an effect, a high-frequency component can be cut off, and erroneous detection of corresponding points due to the influence of a blood flow can be prevented.

In addition, a rotation invariant phase only correlation (RIPOC) may also be employed. In the RIPOC algorithm, a rotation amount estimating process is considered in which, with respect to an image (base boundary line BL) that becomes a base, the degree of rotation of another image (reference boundary line RL) that is a comparison target is detected. More specifically, in a case where an image is rotated, naturally, the frequency component of the image changes. While a change of the phase component is complicated, the amplitude component is rotated in accordance with the rotation of the image, and the change thereof does not depend on the position of the rotation center. Thus, in the RIPOC, focusing on the characteristic of this amplitude component, a polar coordinate image of which the X direction is an angle theta and the Y direction is the radius r is generated by converting the amplitude component into polar coordinates. Then, by performing matching between polar-coordinate images, the deviation in the X direction corresponds to the angle deviation. Accordingly, the rotation amount can be estimated based on a result of the matching, and the original image is corrected by using the estimated rotation amount, and thereafter, the position can be estimated. For example, a method as disclosed in Japanese Patent No. 3574301 may be employed.

In this way, by employing the POC or the RIPOC, a tracking result acquired by a corresponding point search for each pixel of the base boundary line BL can be set as a displacement amount D between the base boundary line BL and the reference boundary line RL. This displacement amount D is a deformation component according to the vertical motion, the parallel motion, and the rotation between the base boundary line BL and the reference boundary line RL.

In addition, while the first to fourth displacement amount calculating processes described above have been described for a case where the displacement amount D (D12) between the base boundary line BL and the reference boundary line RL is acquired as an example, in a case where a plurality of reference boundary lines RL are present, it is apparent that a displacement amount D between the reference boundary lines RL and RL can be acquired.

In the first to fourth displacement amount calculating processes described above, the displacement amount D is acquired so as to approach and match the base boundary line BL not only in a case where the displacement amount D between the base boundary line BL and the reference boundary line RL is acquired, but also in a case where the displacement amount D between the reference boundary lines RL and RL is acquired. In addition, in the first and second displacement amount calculating processes, the displacement amount D may be acquired by subtracting pixels corresponding to each other from each other. Thus, all the first to fourth displacement amount calculating processes described above are processes for acquiring the displacement amount D with the base boundary line BL being set as a displacement base.

<1-3-1-4-5. First Correction Process>

Subsequently, the correction process executed after the displacement amount calculating process will be described.

A first correction process is a process in which the diaphragm boundary line LI is corrected by using a displacement amount D12 calculated using the base boundary line BL as the diaphragm boundary line L1 and using the reference boundary line RL as the diaphragm boundary line L2.

Figure 15:
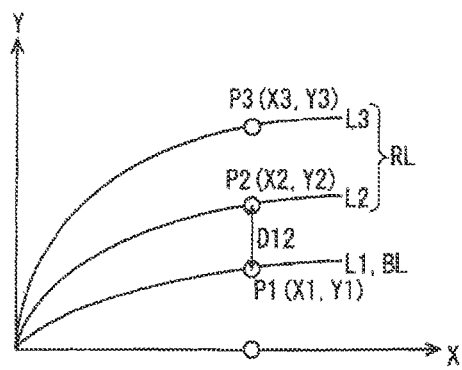
FIG. 15 is a schematic view that illustrates a correction process.

FIG. 15 is a schematic view that illustrates the first correction process. In FIG. 15, for the convenience of description, the displacement amount D of the case of only a vertical motion is assumed, and, as corresponding pixels of the displacement amount D12, pixels P1 and P2 are representatively illustrated.

As illustrated in FIG. 15, first, in a case where the base boundary line BL is the diaphragm boundary line L1, and the reference boundary line RL that is the diaphragm boundary line LI, which is a correction target, is the diaphragm boundary line L2, the displacement amount D12 between the diaphragm boundary lines L1 and L2 is calculated by the first displacement calculating process described above. Then, the diaphragm boundary lines L2 and L3 are corrected by using this displacement amount D12. More specifically, in a case where a displacement-corrected boundary line L2c is acquired by correcting the diaphragm boundary line L2, in other words, the pixel P2 on the diaphragm boundary line L2 becomes a pixel P2c on the displacement-corrected boundary line L2c after the first correction process.

In addition, also in a case where the diaphragm boundary line L3 is corrected by using the displacement amount D12 (the diaphragm boundary line LI that is the correction target is the diaphragm boundary line L3), the pixel P3 on the diaphragm boundary line L3 becomes a pixel P3c on the displacement-corrected boundary line L3c after the first correction process.

By executing the first correction process described above, displacement-corrected boundary lines L2c to L5c (LIc) illustrated in FIG. 12 described above are acquired.

In the example described above, while the first correction process using the displacement amount D12 between the diaphragm boundary lines L1 and L2 acquired by the first displacement amount calculating process has been illustrated, it is apparent that the first correction process may be executed using the displacement amount D12 between the diaphragm boundary lines L1 and L2 acquired by the second to fourth displacement amount calculating processes.

<1-3-1-4-6. Second Correction Process>

A second correction process is a process in which the diaphragm boundary line LI is corrected by using a displacement amount D1I calculated using the base boundary line BL as the diaphragm boundary line L1 and using the reference boundary line RL as the diaphragm boundary line LI (here, an argument I is an integer of two or more).

Figure 16:
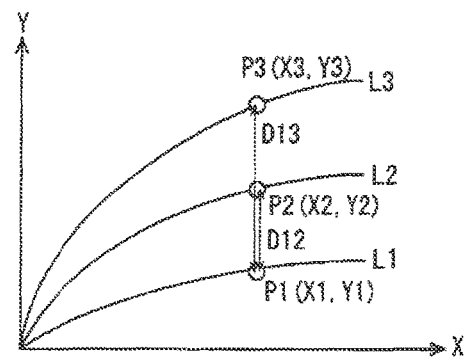
FIG. 16 is a schematic view that illustrates a correction process.

FIG. 16 is a schematic view that illustrates the second correction process. In FIG. 16, for the convenience of description, the displacement amount D of the case of only a vertical motion is assumed, and, as corresponding pixels of the displacement amount D12, pixels P1 and P2 are representatively illustrated, and, as corresponding pixels of a displacement amount D13, the pixel P1 and the pixel P3 are representatively illustrated.

As illustrated in FIG. 16, first, in a case where the base boundary line BL is the diaphragm boundary line L1, and the reference boundary line RL, which is a correction target, is the diaphragm boundary line L2, the displacement amount D12 between the diaphragm boundary lines L1 and L2 is calculated by the first displacement calculating process described above. Then, the diaphragm boundary line L2 is corrected by using this displacement amount D12. More specifically, similar to the description presented above, the pixel P2 on the diaphragm boundary line L2 becomes a pixel P2c on the displacement-corrected boundary line L2c after the second correction process.

In addition, when the diaphragm boundary line L3 is corrected by using the displacement amount D13 between the base boundary line BL and the diaphragm boundary line L3 (in a case where the diaphragm boundary line LI that is the correction target is the diaphragm boundary line L3), the pixel P3 on the diaphragm boundary line L3 becomes a pixel P3c on the displacement-corrected boundary line L3c after the second correction process.

Figure 17A:
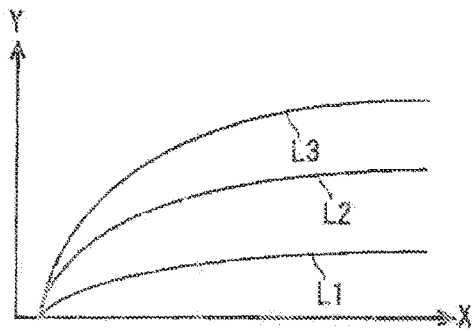
FIG. 17 is a schematic view that illustrates a correction process.
Figure 17B:
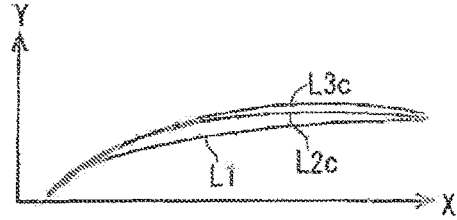

FIG. 17 is a schematic view that illustrates before and after the second correction process. FIG. 17A illustrates the diaphragm boundary lines L2 and L3 before the process (the diaphragm boundary line LI is the correction target), and FIG. 17B illustrates the base boundary line BL (diaphragm boundary line L1) and displacement-corrected boundary lines L2c and L3c after the correction process.

By executing the second correction process described as above, as illustrated in FIG. 17B, a correction result is acquired in which the displacement-corrected boundary lines L2c and L3c approach and match the base boundary line BL (diaphragm boundary line L1) that is the displacement base.

A correction process including the first and second correction processes described above is as follows. In the correction process, a displacement amount calculating process in which, by using a pixel corresponding to a target area boundary line, for one or more of target area boundary lines other than the base boundary line BL (L1) among a plurality of the target area boundary lines (diaphragm boundary lines L1 to L3), a displacement amount ΔD (D12 or D12 and D13) is calculated using the base boundary line BL as a displacement base is executed, the displacement amount ΔD is set as a removal-required component, and two (a predetermined number of) target area boundary lines L2 and L3 other than the base boundary line BL are corrected by using the displacement amount ΔD after the displacement amount calculating process.

In the first correction process, the displacement amount ΔD used for the correction process is the displacement amount D12 between pixels corresponding to the base boundary line and one (diaphragm curve L2) among target area boundary lines. A process in which target area boundary lines (diaphragm curve L2) other than the one target area boundary line are corrected by using this displacement amount D12 is the first correction process.

Meanwhile, in the second correction process, the displacement amounts ΔD used for the correction process are displacement amounts D12 and D13 between corresponding pixels of the base boundary line BL (L1) and one or more (diaphragm curves L2 and L3) of the target area boundary lines. A process in which two (a predetermined number of) target area boundary lines (diaphragm curves L2 and L3) other than the base boundary line BL are corrected by using these displacement amounts D12 and D13 is the second correction process.

<1-3-1-5. Image Generating Unit 150 and Display Unit 34>

The image generating unit 150 generates displacement-corrected boundary line information LG for display based on a second number, which is the first number or less, of the displacement-corrected boundary lines LIc (see FIG. 3). As the displacement-corrected boundary line information LG, the second number of separate images that are separated for each of the second number of the displacement-corrected boundary lines LIc or may generate one still image such that the second number of the displacement-corrected boundary lines LIc are displayed in an overlapping manner.

In addition, it is preferable that information indicating the base boundary line BL is included in the displacement-corrected boundary line information LG.

Then, the display unit 34 displays the displacement-corrected boundary line information LG generated by the image generating unit 150 (see FIG. 3). In other words, in a case where separate images are generated, the display unit 34 sequentially displays the second number of the separate images as the displacement-corrected boundary line information LG. On the other hand, in a case where a still image is generated, the display unit 34 displays one still image as the displacement-corrected boundary line information LG.

Figure 18A:
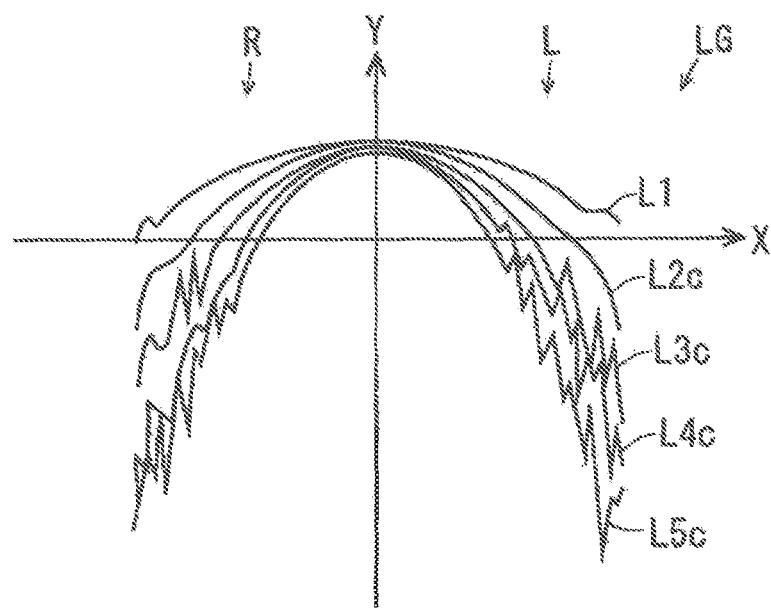
FIG. 18 is a diagram that illustrates displacement-corrected boundary line information for a healthy person as an example.
Figure 18B:
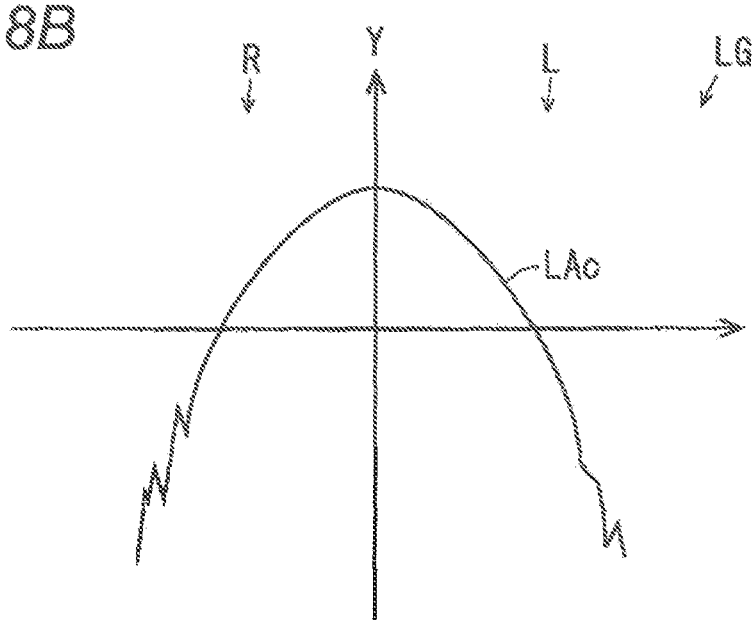
Figure 19A:
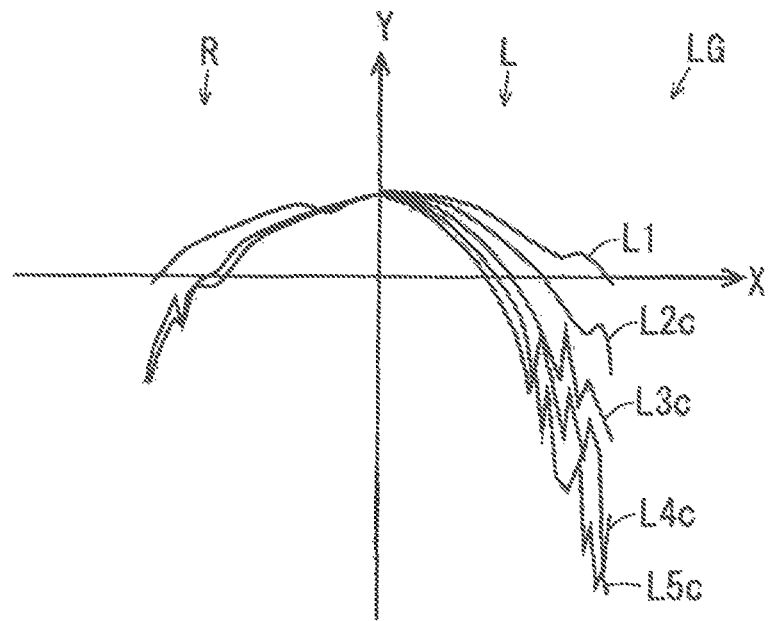
FIG. 19 is a diagram that illustrates displacement-corrected boundary line information for an unhealthy person as an example.

FIGS. 18 and 19 are schematic views that illustrate the displacement-corrected boundary line information LG as an example. FIG. 18 illustrates the displacement-corrected boundary line information LG for a healthy person, and FIG. 19 is a diagram that illustrates the displacement-corrected boundary line information LG for an unhealthy person. In addition, FIGS. 18A and 19A illustrate a case where the image generating unit 150 generates one still image (the displacement-corrected boundary line information LG for display) by changing the color for each boundary line such that the displacement-corrected boundary lines LIc are displayed in an overlapping manner based on the displacement-corrected boundary lines L2c to L5c (LIc) of which the second number of "4" and displays the generated still image on the display unit 34. In addition, similar to the example illustrated in FIGS. 18A and 19A, information indicating the base boundary line BL may be included inside the displacement-corrected boundary line information LG so as to simultaneously display the diaphragm boundary line L1 that is the base boundary line BL in an overlapping manner.

Figure 19B:
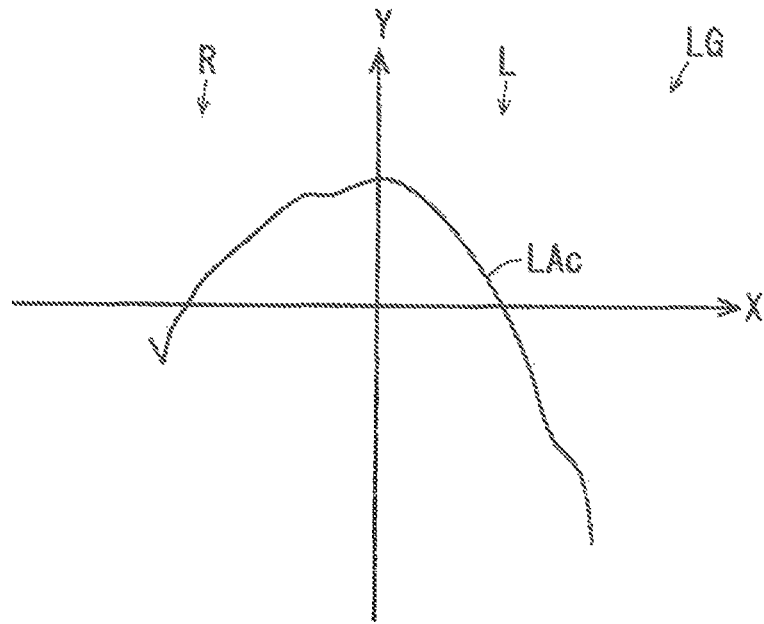

On the other hand, FIGS. 18B and 19B illustrate a case where the image generating unit 150 generates an average displacement-corrected boundary line LAc calculated based on the displacement-corrected boundary lines L2c to L5c as the displacement-corrected boundary line information LG for display and displays the generated average displacement-corrected boundary line on the display unit 34.

As illustrated in FIGS. 18A and 19A, in the displacement-corrected boundary lines L2c to L5c, the deformation due to the vertical motion, the parallel motion, and the rotation of (ii) described above is removed, and only the shape deformation of (i) described above is represented. In other words, like the diaphragm boundary lines L1 to L5 illustrated in FIG. 7, not the whole change in the pulmonary field but a partial abnormality of the shape can be represented.

In addition, in FIG. 18A, the shape of the left side L and the right side R (in other words, the shape of the left pulmonary field and the right pulmonary field) is horizontally symmetrical. However, in FIG. 19A, the displacement-corrected boundary lines L2c to L5c on the right side R of the diaphragm are at the almost same positions, and the shape of the left side L and the right side R of the diaphragm is asymmetrical. By displaying the displacement-corrected boundary line LIc in this way, in the case of a healthy examinee M, as illustrated in FIG. 18A, a shape that is horizontally symmetrical is displayed in a regular radial pattern. However, in the case of an examinee M who has suffered from illness, a deformed shape suggesting an abnormality in part is displayed. For this reason, instead of making a diagnosis based on the user's subjectivity, an objective diagnosis can be made.

Furthermore, as illustrated in FIGS. 18B and 19B, one line that is based on an average value can be output and displayed. Thus, as the user examines the average displacement-corrected boundary line LAc, the shape of the displacement-corrected boundary lines L2c to L5c can be diagnosed comprehensively.

In the example of the displacement-corrected boundary line information LG described above, while one still image has been described to be generated such that the displacement-corrected boundary lines LIc are displayed, separate images separated for each displacement-corrected boundary line LIc may be generated. In other words, in the case of the examples illustrated in FIGS. 18 and 19, by generating four separate images separated for each of the displacement-corrected boundary lines L2c to L5c, the separate images may be sequentially displayed as a dynamic image. In addition, only designated displacement-corrected boundary lines LIc may be displayed.

In addition, the image generating unit 150, based on the displacement-corrected boundary line LIc may calculate a degree of variations (for example, dispersion/a total distance difference, an average, a maximal distance difference, or the like) among the displacement-corrected boundary lines LIc and display the degree of variations as the displacement-corrected boundary line information LG on the display unit 34. For example, the displacement-corrected boundary line information LG may be displayed as two displacement-corrected boundary lines LIc having highest degrees of variations, or only displacement-corrected boundary lines LIc of which the degrees of variations are a threshold or more may be displayed.

<1-4. Basic Operation of Image Processing Device 3>

Figure 20:
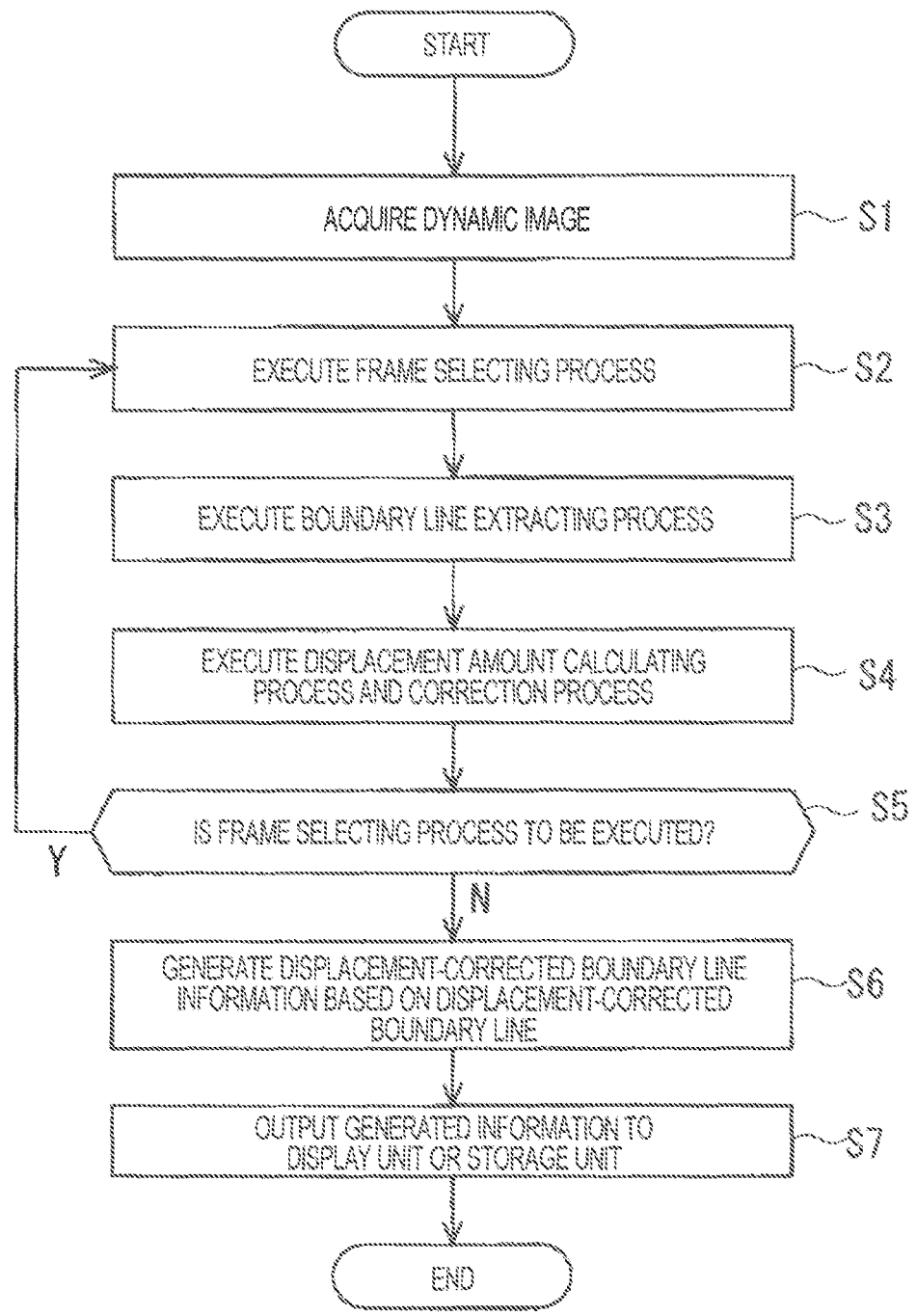
FIG. 20 is a flowchart that illustrates the basic operation of an image processing device 3 realized according to the first embodiment.

FIG. 20 is a flowchart that illustrates the basic operation realized in the image processing device 3 according to this embodiment. The individual function of each unit has already been described (see FIG. 3), here, only the whole process will be described.

As illustrated in FIG. 20, first, in Step S1, the dynamic image acquiring unit 110 of the control unit 31 acquires a dynamic image (a plurality of frame images MI) photographed by the reading control device 14 of the photographing apparatus 1 through the photographing control device 2.

In Step S2, the frame selecting unit 120 executes the frame selecting process including the process of selecting the base frame image BF used for extracting the base boundary line BL and the reference frame images RF used for extracting a predetermined number of diaphragm boundary lines LI other than the base boundary line BL for the selection target frame images TI (see FIG. 3). In the example illustrated in FIG. 7, the frame image T1 is selected as the base frame image BF, and frame images T2 to T5 are selected as the reference frame images RF.

In Step S3, in the boundary line extracting unit 130 executes the boundary line extracting process for acquiring the diaphragm boundary lines LI (in other words, the base boundary line BL and the reference boundary lines RL) by extracting boundary lines of the diaphragm for the base frame image BF and the reference frame images RF (the diaphragm boundary line LI that is the correction target) selected in Step S2 (see FIGS. 6 and 7). In the example illustrated in FIG. 7, the diaphragm boundary line L1 is extracted as the base boundary line BL and the diaphragm boundary lines L2 to L5 are extracted as the reference boundary lines RL that are the diaphragm boundary lines LI of the correction targets.

In Step S4, the displacement correcting unit 140, by using pixels corresponding to the base boundary line BL and the reference boundary lines RL extracted in Step S3, executes the displacement amount calculating process (any one of the first to fourth displacement amount calculating processes) for calculating a displacement amount D of the reference boundary line RL by using the base boundary line BL as a displacement base and then executes the correction process for correcting the diaphragm boundary line LI that is the correction target by using the displacement amount D. Accordingly, the displacement-corrected boundary lines LIc from which the removal-required component (the deformation component of a vertical motion, a parallel motion, rotation, or the like) is removed are acquired (FIGS. 12 and 17B)).

In Step S5, in a case where the process is further executed by the displacement correcting unit 140, when the reference boundary line RL (the diaphragm boundary line LI that is the correction target) is changed, the displacement correcting unit 140 instructs the frame selecting unit 120 to change the reference frame images RF (the frame images that are the correction targets), and the process of Steps S2 to S4 is repeated again. On the other hand, in a case where the process is ended by the displacement correcting unit 140, the process proceeds to Step S6.

In other words, in Step S2, as illustrated in FIG. 15, in a case where the reference frame images RF (frame images that are correction targets) are frame images T2 and T3, and the frame images T2 and T3 are selected together (in other words, the reference boundary lines RL are the diaphragm boundary lines L2 and L3), the process proceeds to Step S6. However, in a case where the frame images T2 and T3 are individually selected instead of being selected together as the reference frame images RF (in other words, in a case where the diaphragm boundary lines L2 and L3 as the reference boundary lines RL are not processed together), when the reference frame image RF is changed, the process proceeds to Step S2, and the process of Steps S2 to S4 is executed.

In Step S6, the image generating unit 150 generates the displacement-corrected boundary line information LG based on the displacement-corrected boundary lines LIc acquired in Step 4 (see FIGS. 18 and 19).

In the displacement-corrected boundary line information LG, at least information indicating the displacement-corrected boundary lines LIc is included, and it is preferable to also include information indicating the base boundary line BL therein.

Finally, in Step S7, the image generating unit 150 outputs the displacement-corrected boundary line information LG generated in Step S6 to the display unit 34 or the storage unit 32 (see FIG. 3), and the flow of this operation ends.

As above, in the image processing device 3 according to the first embodiment, the displacement amount calculating process is executed in which, by using pixels corresponding to the first number of (a plurality of) diaphragm boundary lines LI (a plurality of target area boundary lines), a displacement amount D acquired by using the base boundary line BL as a displacement base is calculated for one or more diaphragm boundary lines LI other than the base boundary line BL among the first number of diaphragm boundary lines LI (a plurality of reference boundary lines RL). Here, the displacement amount D represents a removal-required component. Then, by executing the correction process for correcting a predetermined number (the second number) of diaphragm boundary lines LI other than the base boundary line BL by using the displacement amount D after the displacement amount calculating process, the second number (predetermined number) of displacement-corrected boundary lines LIc in which the removal-required component is removed are acquired, and the displacement-corrected boundary line information LG for display that is based on the second number (predetermined number) of the displacement-corrected boundary lines LIc is displayed on the display unit 34. In other words, by displaying the displacement-corrected boundary lines LIc acquired by removing the deformation corresponding to the displacement amount D from the diaphragm boundary lines LI, the user perceives a change in the shape of the diaphragm boundary line LI, whereby the motion of the shape of the diaphragm can be perceived. In addition, since the shape of the diaphragm boundary line LI can be perceived, a partial abnormality of the shape can be found, and the partial abnormality such as adhesion can be easily diagnosed. Furthermore, since the diagnosis content desired by the user is collected in the displacement-corrected boundary line information LG, a minimum requisite diagnosis time is necessary, whereby the efficiency of the diagnosis is improved. For this reason, a dynamic-state diagnosis can be executed appropriately and efficiently.

In addition, the removal-required component includes at least one component among deformation components according to a vertical motion, a parallel motion, and rotation in the target area, and accordingly, the displacement-corrected boundary lines LIc acquired by removing the deformations due to the vertical motion, the parallel motion, and the rotation from the diaphragm boundary lines LI can be displayed.

Furthermore, the frame selecting unit 120 is further included which executes, for selection target frame images TI including at least a plurality of frame images MI, the frame selecting process including the process of selecting the base frame image BF used for extracting the base boundary lines BL and the reference frame images RF used for extracting the diaphragm boundary lines LI other than the base boundary line BL, and the displacement calculating process includes the process of calculating a displacement amount D between corresponding pixels of the diaphragm boundary lines RL of the reference frame image RF by using the diaphragm boundary line LI of the base frame image BF as the base boundary line BL. Accordingly, frame images corresponding to user's diagnosis purpose can be selected, and the displacement-corrected boundary line information LG corresponding to the diagnosis purpose can be displayed. In addition, by selecting only necessary frame images, compared to the case where the displacement-corrected boundary lines LIc are acquired for all the frame images MI included in the dynamic image, a calculation time required for the boundary line extracting process, the displacement amount calculating process, and the correction process can be minimized.

In addition, the second number (predetermined number) of separate images separated for each of the second number (predetermined number) of displacement-corrected boundary lines LIc are generated, and the second number (predetermined number) of separate images are sequentially displayed as the displacement-corrected boundary line information LG. Accordingly, a change of the shape of the diaphragm boundary line LI can be perceived from the dynamic image.

Furthermore, one still image is generated, and the one still image is displayed as the displacement-corrected boundary line information LG such that the second number (predetermined number) of displacement-corrected boundary lines LIc are displayed in an overlapping manner. For example, in a case where the shape of the second number (predetermined number) of the displacement-corrected boundary lines LIc set as diagnosis targets is used as the displacement-corrected boundary line information LG, the displacement-corrected boundary lines LIc can be displayed to be identifiable in an overlapping manner. Accordingly, a change of the shape of the diaphragm boundary line LI can be perceived on one still image.

In addition, since the target area is the diaphragm area, diseases such as pulmonary emphysema and diaphragmatic eventration can be appropriately diagnosed through a dynamic-state diagnosis. In such a disease, in the case of a minor symptom, while the abnormality may not be noticed, by making a diagnosis using the displacement-corrected boundary line information LG, the diagnosis does not depend on the user's subjectivity, whereby an erroneous diagnosis can be prevented.

2. Second Embodiment

In an image processing device according to a second embodiment of the present invention, a displacement correcting unit is different from that of the image processing device 3 according to the first embodiment in points to be described below. In addition, the remaining configuration is similar to that of the image processing device 3.

<2-1. Displacement Correcting Unit>

Hereinafter, a correction process executed by the displacement correcting unit according to the second embodiment will be referred to as a third correction process. A displacement amount D used for the third correction process is a displacement amount from a diaphragm boundary line LI that is nearest in time to a diaphragm boundary line LI that is a correction target.

Figure 21:
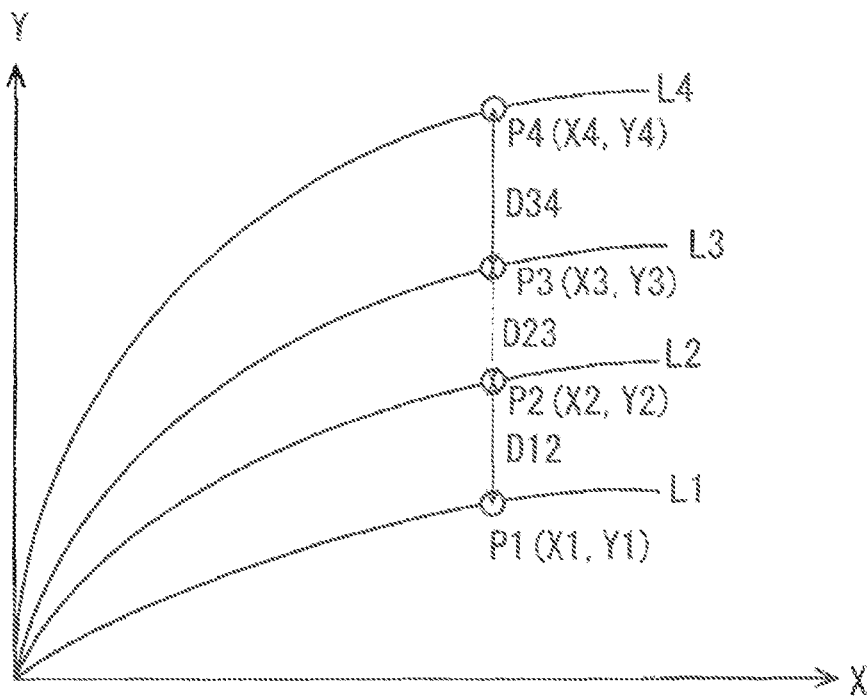
FIG. 21 is a schematic view that illustrates a correction process according to a second embodiment.

FIG. 21 is a schematic view that illustrates the third correction process. In FIG. 21, for diaphragm boundary lines L1 to L4, for the convenience of description, a displacement amount D of the case of only a vertical motion is assumed, and, as corresponding pixels of a displacement amount D12, pixels P1 and P2 are representatively illustrated, as corresponding pixels of a displacement amount D23, the pixel P2 and a pixel P3 are representatively illustrated, and, as corresponding pixels of a displacement amount D34, the pixel P3 and a pixel P4 are representatively illustrated.

As illustrated in FIG. 21, first, in a case where a base boundary line BL is a diaphragm boundary line L1, and a diaphragm boundary line LI, which is a correction target, in other words, a reference boundary line RL is a diaphragm boundary line L2, similar to the second correction process, the diaphragm boundary line L2 is corrected by using the displacement amount D12 between the diaphragm boundary lines L1 and L2. More specifically, similar to the description presented above, the pixel P2 on the diaphragm boundary line L2 becomes a pixel P2c on the displacement-corrected boundary line L2c after the third correction process.

Next, when a diaphragm boundary line LI that is a correction target is the diaphragm boundary line L3, a comparison target for which the displacement amount is acquired is changed to the diaphragm boundary line L2, and the diaphragm boundary line L3 is corrected using the displacement amount D23. In such a case, the pixel P3 on the diaphragm boundary line L3 becomes a pixel P3c on the displacement-corrected boundary line L3c after the third correction process.

Furthermore, when a diaphragm boundary line LI that is a correction target is the diaphragm boundary line L4, a comparison target for which the displacement amount is acquired is changed to the diaphragm boundary line L3, and the diaphragm boundary line L4 is corrected using the displacement amount D34 between the diaphragm boundary lines L3 and L4. At this time, the pixel P4 on the diaphragm boundary line L4 becomes a pixel P4c on the displacement-corrected boundary line L4c after the third correction process.

As above, in the image processing device according to the second embodiment, the displacement amount D used for the correction process is a displacement amount D from the diaphragm boundary line LI that is nearest in time from the diaphragm boundary line LI that is a correction target.

Thus, by executing the third correction process constantly using the displacement amount D between the diaphragm boundary lines LI of selection target frame images TI that are nearest to each other, displacement-corrected boundary lines L2c to L4c having high correction accuracy can be acquired. As a result, the displacement-corrected boundary line information LG that is suitable for the diagnosis purpose can be displayed, and accordingly, the dynamic-state diagnosis can be executed more appropriately and efficiently.

3. Third Embodiment

In an image processing device according to a third embodiment of the present invention, a displacement correcting unit is different from that of the image processing device 3 according to the first embodiment in points to be described below. In addition, the remaining configuration is similar to that of the image processing device 3.

<3-1. Displacement Correcting Unit>

Hereinafter, a correction process executed by the displacement correcting unit according to the third embodiment will be referred to as a fourth correction process. In a case where at least one diaphragm boundary line LI is present between a base boundary line BL to a diaphragm boundary line LI that is a correction target, a displacement amount D used for the fourth correction process is a displacement amount D between the base boundary line BL to the diaphragm boundary line LI, which is the correction target, that is acquired as a sum of displacement amounts D between two boundary lines LI that are adjacent in time.

Figure 22:
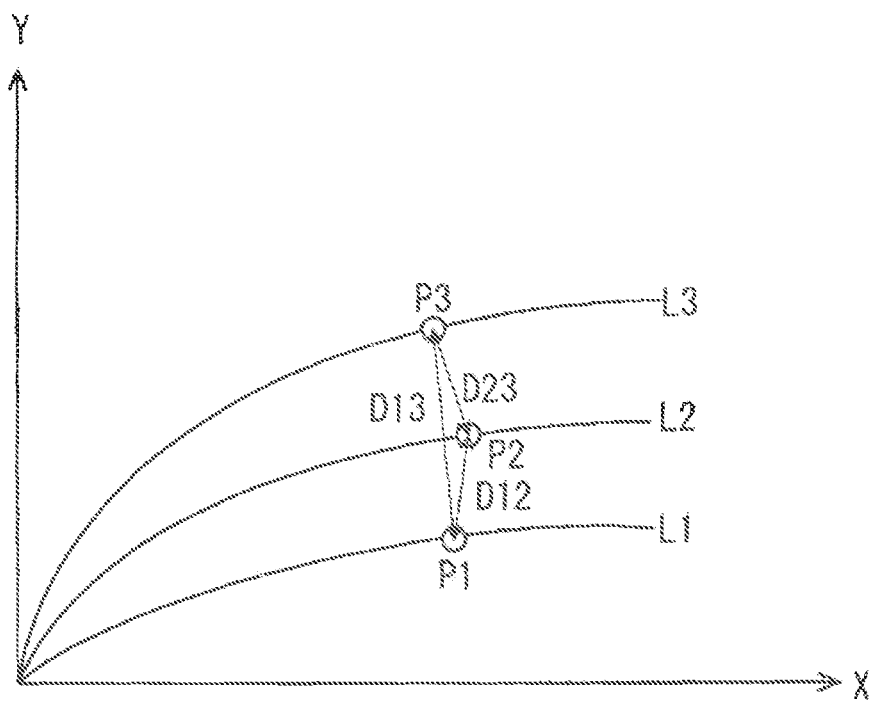
FIG. 22 is a schematic view that illustrates a correction process according to a third embodiment.

FIG. 22 is a schematic view that illustrates the fourth correction process. In FIG. 22, for diaphragm boundary lines L1 to L3, for the convenience of description, as corresponding pixels of a displacement amount D12, pixels P1 and P2 are representatively illustrated, as corresponding pixels of a displacement amount D23, the pixel P2 and a pixel P3 are representatively illustrated, and, as corresponding pixels of a displacement amount D13, the pixel P1 and the pixel P3 are representatively illustrated.

As illustrated in FIG. 22, a case will be described in which the diaphragm boundary line LI that is a correction target is the diaphragm boundary line L3, and a correction is made using the displacement amount D13. In the fourth correction process, in a displacement amount calculating process, the displacement amount D13 is calculated with being subdivided into the displacement amount D12 and the displacement amount D23, and a displacement amount (D12+D23) acquired by adding both the displacement amounts D is used as a displacement amount between the diaphragm boundary lines L1 and L3. For this reason, first, by the displacement amount calculating process, the displacement amount D12 between the diaphragm boundary line L1 and the diaphragm boundary line L2 is calculated, and the displacement amount D23 between the diaphragm boundary line L2 and the diaphragm boundary line L3 is calculated. In this way, in the displacement amount calculating process, (D12+D23) is calculated.

In other words, when the displacement amount D13 is calculated, compared to the displacement amount D13 that is directly acquired between the diaphragm boundary line L1 and the diaphragm boundary line L3, similar to the first and second embodiments, in the displacement amount (D12+D23) calculated in this embodiment, the displacement amount acquired through the diaphragm boundary line L2 is included, and accordingly, the route in which the diaphragm boundary lines L1 to L3 are displaced is reflected, and the accuracy is high.

In this way, in the fourth correction process, the diaphragm boundary line L3 is corrected using the displacement amount (D12+D23) calculated with high accuracy, and the displacement-corrected boundary line L3c is calculated more accurately as well. In other words, the pixel P3 on the diaphragm boundary line L3 becomes a pixel P3c on the displacement-corrected boundary line L3c after the fourth correction process.

<3-2. Basic Operation>

In the basic operation of the image processing device according to the third embodiment, Steps S2 to S4 illustrated in FIG. 20 are different from those of the first embodiment. In other words, in Step S2 of the first embodiment, while the frame selecting unit 120 executes the frame selecting process between the base frame image BF and the reference frame image RF, in Step S2 of the third embodiment, in addition thereto, a frame image (hereinafter, referred to as an "intermediate frame image") present between the photographing timing of the base frame image BF and the photographing timing of the reference frame image RF is also selected, which is different from the first embodiment. In other words, in the example illustrated in FIG. 22 in which the displacement amount D13 is calculated, a frame image T1 is selected as the base frame image BF, and a frame image T3 is selected as the reference frame image RF, and a frame image T2 is also selected as the intermediate frame image present between such photographing timings.

Then, in Step S3 of the third embodiment, the boundary line extracting process is executed also for the intermediate frame image in addition to the base frame image BF and the reference frame image RF.

In addition, in Step S4 of the third embodiment, a displacement amount calculating process is executed in which a displacement amount D of the reference boundary line RL with respect to the base boundary line BL is calculated by using the diaphragm boundary line of the intermediate frame image, and then a correction process is executed in which the diaphragm boundary line LI that is a correction target is corrected by using the displacement amount D (see FIG. 22).

As above, in the image processing device according to the third embodiment, the displacement amount D used for the correction process is a displacement amount D between the base boundary line BL to the diaphragm boundary line LI, which is a correction target, that is acquired as a sum of displacement amounts D between two boundary lines LI adjacent in time. In this way, in the displacement amount calculating process, one displacement amount D between the base boundary line BL and the diaphragm boundary line LI is subdivided and calculated, and accordingly, compared to the displacement amount D calculated without subdividing the base frame image BF to the reference frame image RF, the displacement amount can be calculated with high accuracy.

4. Fourth Embodiment

Figure 23:
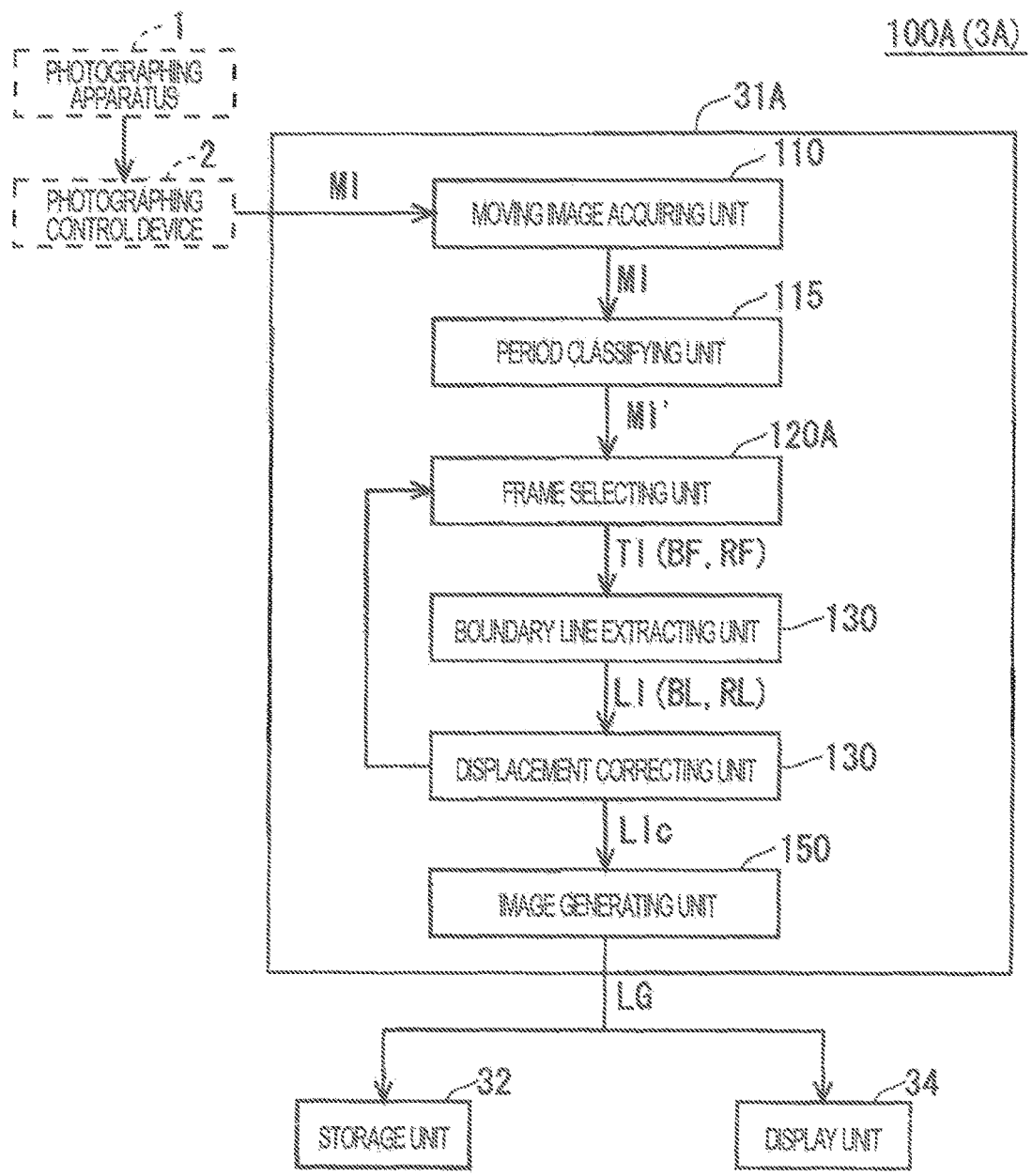
FIG. 23 is a block diagram that illustrates the functional configuration of an image processing device 3A according to a fourth embodiment.

FIG. 23 is a diagram that illustrates the functional configuration of a control unit 31A used by an image processing device 3A according to a fourth embodiment. This control unit 31A is used as a substitute for the control unit 31 (see FIG. 3) of the image processing device 3 according to the first embodiment. A difference from that of the first embodiment is that the control unit 31A further includes a period classifying unit 115. Thus, in accordance therewith, the frame selecting unit 120 is changed to a frame selecting unit 120A. The remaining configuration is similar to that of the image processing device 3.

<4-1. Period Classifying Unit 115>

The period classifying unit 115 detects a so-called respiration period (target area period) in which the diaphragm of the examinee M (body) synchronized with the photographing time, at which a plurality of frame images MI are photographed by the dynamic image acquiring unit 110, periodically changes and classifies the plurality of frame images MI in units of the respiration periods (units of target area periods). Then, the period classifying unit 115 outputs a plurality of frame images MI' after the classification in units of the respiration periods to the frame selecting unit 120 (see FIG. 23).

When the respiration period of the examinee M is detected, the period classifying unit 115 executes a respiratory information acquiring process for acquiring respiratory information and detects a respiration period PC, an inhalation phase PH1 and an exhalation phase PH2 based on the respiratory information. Hereinafter, the respiratory information acquiring process and the detection of the respiration period and the like will be described.

<4-1-1. Respiratory Information Acquiring Process>

When a physical state value defined as a value representing a physical state of the diaphragm area that changes in time is referred to as a respiration vibration value, the respiratory information acquiring process is a process in which a respiration vibration value is calculated based on a plurality of frame images MI configuring a dynamic image acquired by the dynamic image acquiring unit 110, and the respiration vibration value is set as the respiratory information (see FIG. 23).

As illustrated in FIG. 23, first, in the respiratory information acquiring process, the respiration vibration value is calculated by using the plurality of frame images MI acquired by the dynamic image acquiring unit 110. More specifically, the respiration vibration value is an index used for measuring a change in the size of the pulmonary field area according to respiration, and examples thereof include a "distance between characteristic points of the pulmonary field area (a distance from the pulmonary apex to the diaphragm or the like)", an "area value (the size of the pulmonary field area) of the pulmonary field part", the "absolute position of the diaphragm", and a "pixel density value of the pulmonary field area", and the like. Hereinafter, a case will be described as an example in which the respiration vibration value is the "area value of the pulmonary field part" and the "distance between characteristic points of the pulmonary field area".

In a case where the respiration vibration value is the "area value of the pulmonary field part", the contour of the pulmonary field part is extracted, and the number of pixels surrounded by the contour may be defined as the area of the pulmonary field part.

Figure 24A:
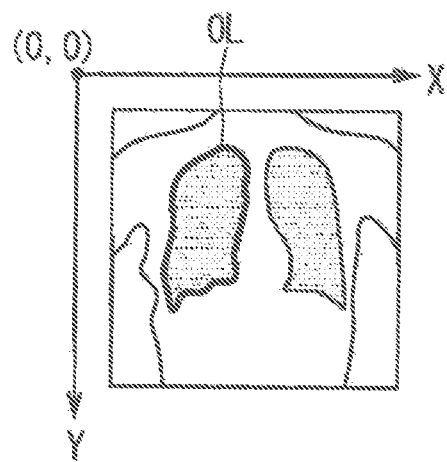
FIG. 24 is a diagram that illustrates a method of calculating a respiration period.
Figure 24B:
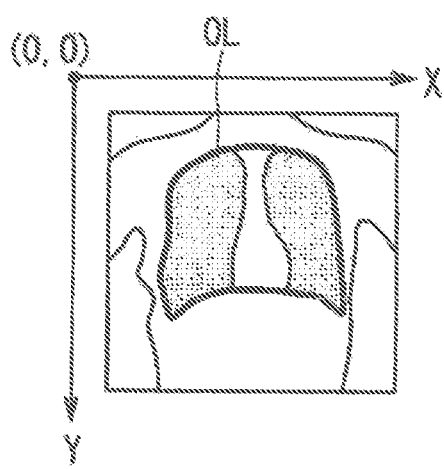

FIGS. 24A and 24B are schematic views that illustrate the extraction of the contour of the pulmonary field part as an example. In the extraction of the pulmonary field part, by using the extraction method described with reference to FIG. 8, each of the left and right sides may be extracted (see FIG. 24A), similar to the case illustrated in FIG. 8, or a contour (see FIG. 24B) including the area of the heart and the spine may be extracted as the pulmonary field part.

In this way, in the respiratory information acquiring process, the contour OL of the pulmonary field part is extracted by using a plurality of acquired frame images MI, and the number of pixels inside the extracted area is detected as the area value of the pulmonary field part, whereby the respiration vibration value is acquired (see FIGS. 24A and 24B).

In a case where the respiration vibration value is the "distance between characteristic points of the pulmonary field area", a distance between characteristic points of the pulmonary field area is calculated by using a plurality of frame images MI. In other words, the pulmonary field part is extracted using a method similar to the method described above, two characteristic points are acquired from the extracted area, and a distance between the two points is acquired, whereby a respiration vibration value is detected. Then, a change in the distance (respiration vibration value) between the characteristic points is set as a respiration phase PH.

Figure 24C:
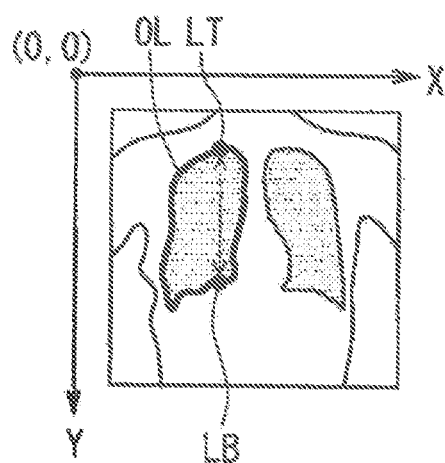
Figure 24D:
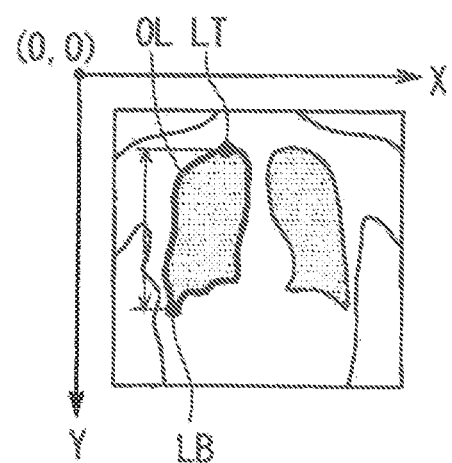

FIGS. 24C and 24D are exemplary diagrams that illustrate the positions of characteristic points of a pulmonary field area in a case where the contour OL of the pulmonary field part illustrated in FIG. 24A is used. In a case where a change in a length (pulmonary field length) from the upper end LT of the pulmonary area to the lower end LB thereof is calculated, the example illustrated in FIG. 24C is an example in which the pulmonary apex is set as the upper end LT of the pulmonary area, and an intersection between a line drawn downward from the pulmonary apex in the body axis direction and the diaphragm is extracted as the lower end LB. The example illustrated in FIG. 24D is an example in which the pulmonary apex is set as the upper end LT of the pulmonary area, and a costophrenic angle is extracted as the lower end LB.

In this way, in the respiratory information acquiring process, by using a plurality of frame images MI that have been acquired, the contour OL of the pulmonary field area is extracted, and a distance between characteristic points is detected based on the extracted area, whereby the respiration vibration value is acquired (see FIGS. 24C and 24D).

Then, as illustrated in FIG. 5 described above, a respiration phase PH in which waveform data of the respiration vibration value acquired in the respiratory information acquiring process is represented in a time series, in other words, a result of monitoring a calculated respiration vibration value such as the area value of the pulmonary field area or the distance between characteristic points for every photographing timing TM in the time direction can be acquired.

In this embodiment, while the respiratory information is acquired by using photographed images, a measurement result acquired using an external device may be used. In such a case, information relating to the respiration period is input from the external device to the period classifying unit 115. As a method for the measurement using the external device, for example, a device as disclosed in Japanese Patent No. 3793102 may be used. In addition, a technique (for example, see "Unrestrained Respiration Monitoring for Sleeping Person Using Fiber Grating Vision Sensor", Aoki Hirooki and Nakajima Masato, Proceedings of the Society Conference of IEICE 2001, Proceedings of the Society Conference of Information System, 320-321, 2001-08-29 or the like) for monitoring using a sensor configured by a laser beam and a CCD camera or the like may be used. In other words, by using a method of detecting the motion of the chest of a subject M by using laser radiation, a respiration monitor belt, or the like or by detecting the air stream of the respiration using an air flow meter, the respiratory information can be acquired, and such methods may be applied.

<4-1-2. Method of Detecting Respiration Period PC, Inhalation Phase PH1, and Exhalation Phase PH2>

Subsequently, a change in the respiration vibration value that is detected in the respiratory information acquiring process is set as the respiration phase PH, and the respiration period PC, the inhalation phase PH1, and the exhalation phase PH2 are detected. More specifically, the inhalation phase PH1 and the exhalation phase PH2 are detected by calculating a maximum value B1 and a minimum value B2 of the respiration vibration value within the respiration period PC (see FIG. 5).

As illustrated in FIG. 5, one period of the respiration period (respiration cycle) PC is configured by inhalation and exhalation and is formed by inhalation executed once and exhalation executed once. In the inhalation, the diaphragm is lowered so as to draw the air into the inside thereof, and accordingly, the area of the pulmonary field in the chest increases. When the air is maximally breathed in (a transition point between inhalation and exhalation), a maximum inhalation phase IM is formed. In the exhalation, as the diaphragm is raised so as to breathe out the air, the area of the pulmonary field decreases, and, when the air is maximally breathed out (a transition point between exhalation and inhalation), a maximum exhalation phase EM is formed. In the example illustrated in FIG. 5, the respiration period PC is set between the maximum values B1, the respiration period PC may be set between minimum values PB2.

Hereinafter, the method of detecting the respiration period PC, the inhalation phase PH1, and the exhalation phase PH2 will be described.

A first method is a method of determining the respiration period PC by sequentially calculating time when the respiration vibration values are a maximum value and a minimum value in the entire time of a dynamic image and determining a maximum value B1 and a minimum value B2 of the respiration vibration value within the respiration period PC. More specifically, in a state in which a high-frequency noise component is decreased by applying smoothing of the respiration vibration value in the entire time, a maximum value (the maximum inhalation phase IM) and a minimum value (the maximum exhalation phase EM) of the respiration vibration value are calculated. Accordingly, it can be prevented that a noise component included in the respiration vibration value is erroneously detected as a maximum value or a minimum value.

A second method is a method of detecting the respiration period PC first and detecting time when the respiration vibration values are a maximum value and a minimum value for every respiration period PC. A difference from the first method is that the maximum value (in other words, the maximum inhalation phase IM) and the minimum value (maximum exhalation phase EM) of the respiration vibration value are calculated not in the entire time but in units of the respiration periods PC. Also in the second method, similar to the first method, the maximum value and the minimum value may be extracted in a state in which the high-frequency noise component is decreased by applying smoothing of the respiration vibration value.

In this way, the period classifying unit 115 sets a change of the respiration vibration value as the respiration phase PH and detects the maximum value B1 and the minimum value B2 of the respiration vibration value within the respiration period PC, thereby detecting the inhalation phase PH1 and the exhalation phase PH2 (see FIG. 5).

<4-2. Frame Selecting Unit 120A>

Since the period classifying unit 115 detects the respiration period PC, the maximum value B1 and the minimum value B2 of the respiration vibration value, the inhalation phase PH1, and the exhalation phase PH2, the frame selecting unit 120A can execute the process as below.

In a case where the base frame image BF and the reference frame image RF are frame images when the respiration period PC is within the same period, as the frame selecting process of (a1) described above in the frame selecting unit 120A, a first selection process and a second selection process described below are executed.

The first selection process is the process of selecting any one frame image from among (b1) a frame image when the respiration vibration value corresponds to a first set value set in advance, (b2) a frame image when the respiration vibration value corresponds to the maximum value B1, and (b3) a frame image when the respiration vibration value corresponds to the minimum value B2 as the base frame image BF.

In addition, the second selection process is the process of selecting any one frame image from among (c1) a frame image when the respiration vibration value corresponds to a second set value set in advance, (c2) a frame image that is adjacent to the base frame image BF in time, (c3) when the base frame image BF is a frame image of (b2), a frame image corresponding to the minimum value B2 of the respiration vibration value, and (c4) when the base frame image BF is a frame image of (b3), a frame image corresponding to the maximum value B1 of the respiration vibration value as the reference frame image RF.

The first set value of (b1) and the second set value of (c1) described here are respiration vibration values that are arbitrary designated by a user. In the first selection process, the selection process is executed using a frame image at the time of the respiration vibration value corresponding to the designated first set value as the base frame image BF. In addition, in the second selection process, the selection process is executed by using a frame image at the time of the respiration vibration value corresponding to the designated second set value as the reference frame image RF. Furthermore, as a premise of the first and second selection processes described above, a condition that the base frame image BF and the reference frame image RF are limited to be within the inhalation phase PH1 or the exhalation phase PH2 may be applied. In addition, to the first and second selection processes described above, a user may arbitrary designate a base frame image BF and a reference frame image RF for frame images within the respiration period PC.

In this way, by using the base frame image BF and the reference frame image RF selected in the first and second selection processes executed by the frame selecting unit 120A, any of the first to fourth boundary line extracting processes is executed, and any of the first to fourth displacement amount calculating process is executed (see FIG. 23).

<4-3. Basic Operation of Image Processing Device 3A>

Figure 25:
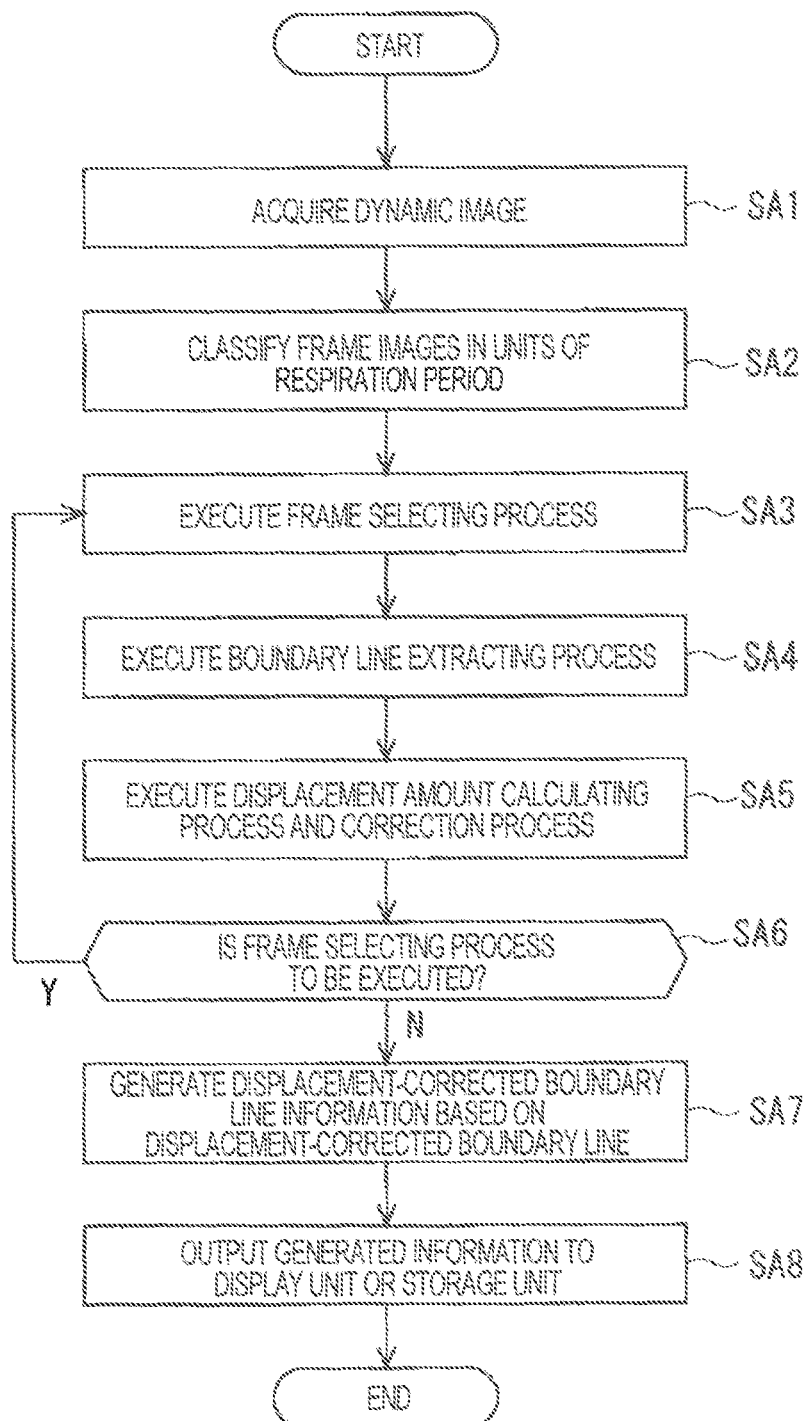
FIG. 25 is a flowchart that illustrates the basic operation of an image processing device 3A realized in a fourth embodiment.

Subsequently, FIG. 25 is a flowchart that illustrates the operation of the image processing device 3A according to the fourth embodiment. In FIG. 25, Steps SA1 and SA4 to SA8 are similar to Steps S1 and S3 to S7 illustrated in FIG. 20, and thus, description thereof will not be presented.

In this fourth embodiment, the period classifying unit 115 that is not provided in the first embodiment is added, and the frame selecting means 120A is substituted for the frame selecting means 120, and only the following processes are changed.

As a process similar to that of the first embodiment, through Step SA1, as illustrated in FIG. 25, in Step SA2, the period classifying unit 115 detects the respiration period PC of an examinee M (body) that is synchronized with the photographing time at which the plurality of frame images MI acquired in Step SA1 and classifies the plurality of frame images MI in units of the respiration periods PC, thereby acquiring a plurality of frame images MI'. At this time, in addition to the respiration period PC, the period classifying unit 115 simultaneously detects the maximum value B1 and the minimum value B2 of the respiration vibration value, the inhalation phase PH1, and the exhalation phase PH2.

In addition, in Step SA3, in consideration of the respiration period PC and the like detected in Step SA2, as the frame selecting process of (a1) described above that is executed by the frame selecting unit 120A, the first selection process and the second selection process are executed, whereby the base frame image BF and the reference frame image RF are selected. The remaining process is similar to that of the first embodiment.

As above, in the image processing device 3A according to the fourth embodiment, the base frame image BF and the reference frame image RF are frame image at the time of the respiration period PC being within the same period, the frame selecting process of (a1) includes a first selection process in which any one frame image of (b1) to (b3) is selected as the base frame image BF, and the second selection process in which any one frame image of any of (c1) to (c4) is selected as a reference frame image RF. Accordingly, between frame images within the same period, which are desired by the user, a change of the shape of the diaphragm boundary line LI can be diagnosed with high accuracy.

5. Fifth Embodiment

In a case where a follow-up observation is made by using dynamic images of an examinee M that are photographed in the past, it is necessary to make a diagnosis by aligning and comparing a plurality of X-ray dynamic images, and the comparison efficiency is low.

Thus, an object of the fifth embodiment is to acquire displacement-corrected boundary line information by using dynamic images of the examinee M of the past and the present. In this embodiment, while "present" and "past" are denoted in the head of terms, here, the meaning of denoting "present" is used as a concept of being new in time compared with denoting "past".

Figure 26:
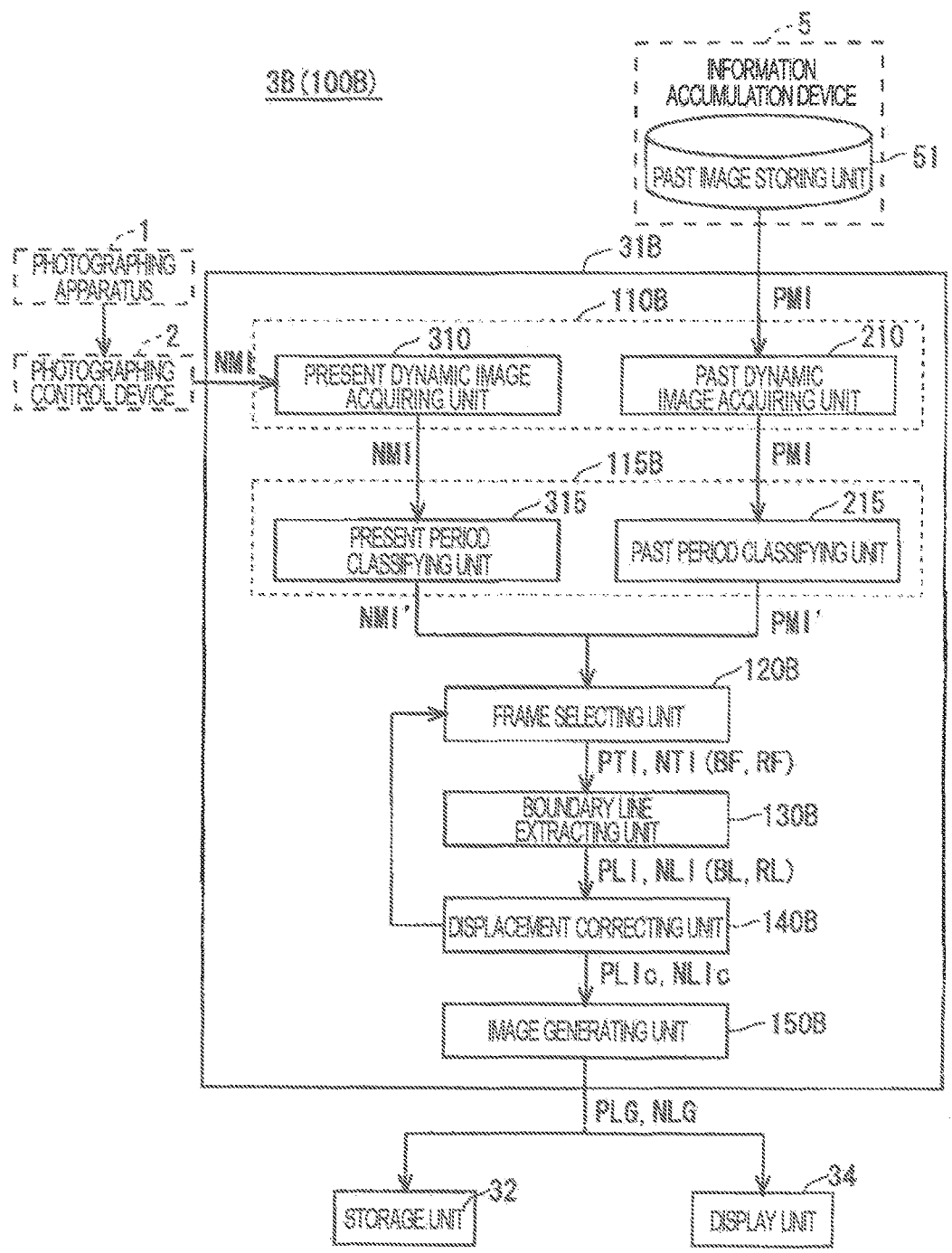
FIG. 26 is a block diagram that illustrates the functional configuration of an image processing device 3B according to a fifth embodiment.

FIG. 26 is a block diagram that illustrates the functional configuration of a control unit 31B used by an image processing device 3B configured as a fifth embodiment of the present invention. This control unit 31B is used as a substitute for the control unit 31 (see FIG. 3) of the image processing device 3 according to the first embodiment. A difference from the first embodiment is that, by using a dynamic image photographed in the past and further including a period classifying unit 115B, the constituent units are changed to a dynamic image acquiring unit 110B, a frame selecting unit 120B, a boundary line extracting unit 130B, a displacement correcting unit 140B, and an image generating unit 150B.

In addition, as illustrated in FIG. 26, information storage device 5 is configured, for example, by a database server using a personal computer or a workstation, is configured to include a past image storage unit (database) 51, and transmits/receives data to/from the control unit 31B through a bus 36 (see FIG. 1). In the past image storing unit 51, dynamic images of the examinee M that are photographed in the past used for a diagnosis are stored in advance. The remaining configuration is similar to that of the image processing device 3.

<5-1. Dynamic Image Acquiring Unit 110B>

The dynamic image acquiring unit 110B, in addition to a present dynamic image acquiring unit 310 that acquires a present dynamic image (a plurality of present frame images NMI) corresponding to the dynamic image acquiring unit 110 described above, is configured to include a past dynamic image acquiring unit 210 that acquires a past dynamic image (a plurality of past frame images PMI) for the same examinee M as that of the present frame image NMI (see FIG. 26).

The past dynamic image acquiring unit 210, for example, as illustrated in FIG. 26 acquires a past dynamic image from the past image storing unit 51. In addition, while it is desirable that the photographing ranges of the present frame images NMI and the past frame images PMI are the same, it is assumed that at least the diaphragm area is necessarily included therein.

In this way, the selection target frame images TI according to the fifth embodiment are configured to include two kinds of frame images including a present frame image NMI and a past frame image PMI photographed for the same examinees M (body) with the photographing periods being separated far from each other.

<5-2. Period Classifying Unit 115B>

The period classifying unit 115B is configured to include a past period classifying unit 215 and a present period classifying unit 315 (see FIG. 26). Here, the past period classifying unit 215 and the present period classifying unit 315 included in the period classifying unit 115B have the same function as that of the period classifying unit 115 described above.

In other words, the present period classifying unit 315 detects a present respiration period of the examinee M synchronized with the photographing time at which a plurality of present frame images NMI acquired by the dynamic image acquiring unit 310 and classifies the plurality of present frame images NMI in units of the present respiration periods. Then, the present period classifying unit 315 outputs a plurality of present frame images NMI' after the classification made in units of the present respiration periods to the frame selecting unit 120B (see FIG. 26).

On the other hand, the past period classifying unit 215 detects a past respiration period of the examinee M synchronized with the photographing time at which a plurality of past frame images PMI acquired by the dynamic image acquiring unit 210 and classifies the plurality of past frame images PMI in units of the past respiration periods. Then, the past period classifying unit 215 outputs a plurality of past frame images PMI' after the classification made in units of the past respiration periods to the frame selecting unit 120B (see FIG. 26).

Figure 27A:
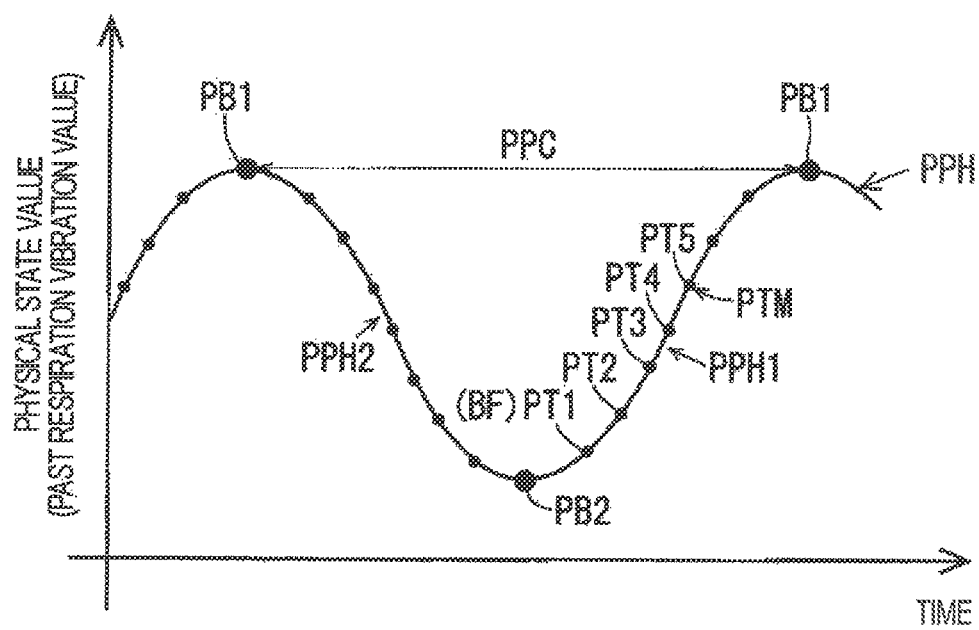
FIG. 27 is a diagram that illustrates a frame selecting process according to the fifth embodiment.
Figure 27B:
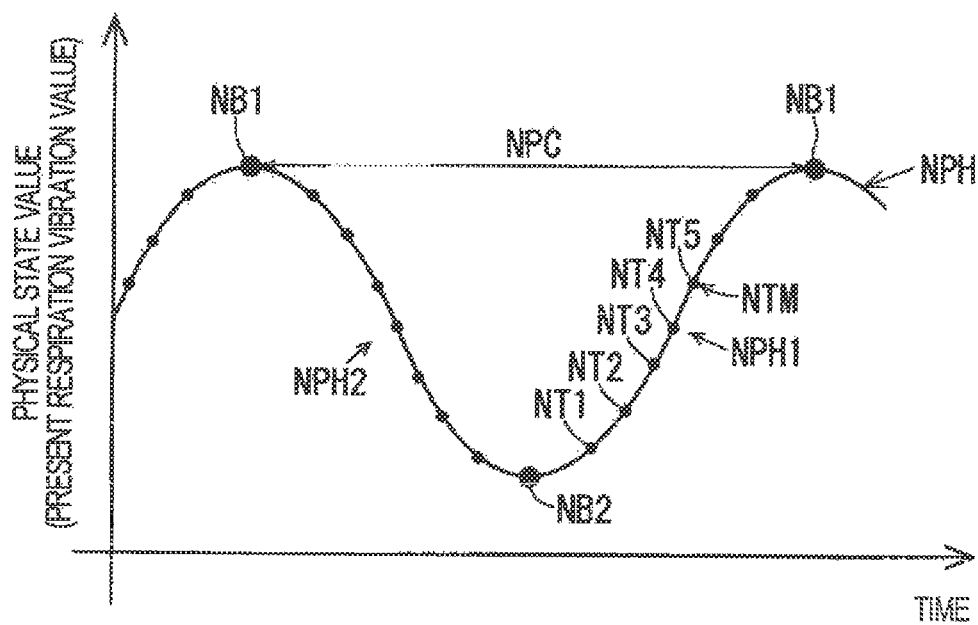

FIG. 27 is a schematic view that illustrates waveform data of the respiration vibration value detected by the period classifying unit 115B in a time series. FIG. 27A is a diagram that illustrates the past respiration phase PPH and the past photographing timing PTM detected by the past period classifying unit 215 altogether, and FIG. 27B is a diagram that illustrates the present respiration phase NPH and the present photographing timing NTM detected by the present period classifying unit 315 altogether.

As illustrated in FIG. 27A, the past period classifying unit 215 detects a past respiration period PPC, a past maximum value PB1 and a past minimum value PB2 of the past respiration vibration value, a past inhalation phase PPH1, and a past exhalation phase PPH2. In addition, as illustrated in FIG. 27B, the present period classifying unit 315 detects a present respiration period NPC, a present maximum value NB1 and a present minimum value NB2 of the present respiration vibration value, a present inhalation phase NPH1, and a present exhalation phase NPH2.

In addition, in the example illustrated in FIG. 27, while the past respiration period PPC (present respiration period NPC) is set between the past maximum values PB1 (present maximum values NB1), the past respiration period may be set between past minimum values PB2 (present minimum values NB2).

<5-3. Frame Selecting Unit 120B>

Since the period classifying unit 115B detects the past respiration period PPC and the like and the present respiration period NPC and the like, the frame selecting unit 120B can execute a process as below.

The frame selecting process executed by the frame selecting unit 120B includes the process of selecting a past frame image PMI (a frame image photographed in the past) as the base frame image BF among the frame images TI (two kinds of frame images including a present frame image NMI and a past frame image PMI).

For example, in the example illustrated in FIG. 27, in the frame selecting process executed by the frame selecting unit 120B, there are ten selection target frame images TI when the selection target frame images are configured by past frame images PT1 to PT5 and the present frame images NT1 to NT5. Then, in the frame selecting process, a base frame image BF is selected from among the five past frame images PT1 to PT5. Then, as the reference frame images RF, the present frame images NT1 to NT5 are selected.

<5-4. Boundary Line Extracting Unit 130B>

The boundary line extracting unit 130B executes a process similar to that of the boundary line extracting unit 130 for the base frame image BF selected by the frame selecting unit 120B and the past frame images PTI and the present frame images NTI corresponding to the reference frame images RF as targets.

For example, in the example illustrated in FIG. 27, since the base frame image BF is one of the past frame images PT1 to PT5, the boundary line extracting unit 130B executes the process for the frame image selected as the base frame image BF among the past frame images PT1 to PT5 and all the present frame images NT1 to NT5. In other words, the base frame image BF is extracted from the past frame images PT1 to PT5, and the present diaphragm boundary lines NL1 to NL5 (NLI) are extracted from the present frame images NT1 to NT5 (see FIG. 26).

<5.5 Displacement Correcting Unit 140B>

The displacement correcting unit 140B executes a process that is similar to that of the displacement correcting unit 140 for the past diaphragm boundary lines PLI and the present diaphragm boundary lines NLI that correspond to the base boundary line BL and the reference boundary lines RL extracted by the boundary line extracting unit 130B.

For example, in the example illustrated in FIG. 27, since the base boundary line BL is constantly the past diaphragm boundary line PL1, and the reference boundary line RL is one of the present diaphragm boundary lines NL1 to NL5, the displacement correcting unit 140B executes an appropriate process by using the present diaphragm boundary lines NL1 to NL5. In other words, present displacement-corrected boundary lines NL1c to NL5c (NLIc) can be acquired based on the present diaphragm boundary lines NL1 to NL5 by using the diaphragm boundary line PL1 as the displacement base (see FIG. 26).

<5-6. Image Generating Unit 150B>

The image generating unit 150B executes a process similar to that of the image generating unit 150 for each of the past displacement-corrected boundary line PLIc and the present displacement-corrected boundary line NLIc acquired by the displacement correcting unit 140B.

For example, in the example illustrated in FIG. 27, since the present displacement-corrected boundary line NLIc is the present displacement-corrected boundary lines NL1c to NL5c, the image generating unit 150B executes the process for each of the present displacement-corrected boundary lines NL1c to NL5c. In other words, the present displacement-corrected boundary line information NLG is acquired from the present displacement-corrected boundary lines NL1c to NL5c (see block diagram of FIG. 26).

<5-7. Basic Operation of Image Processing Device 3B>

Figure 28:
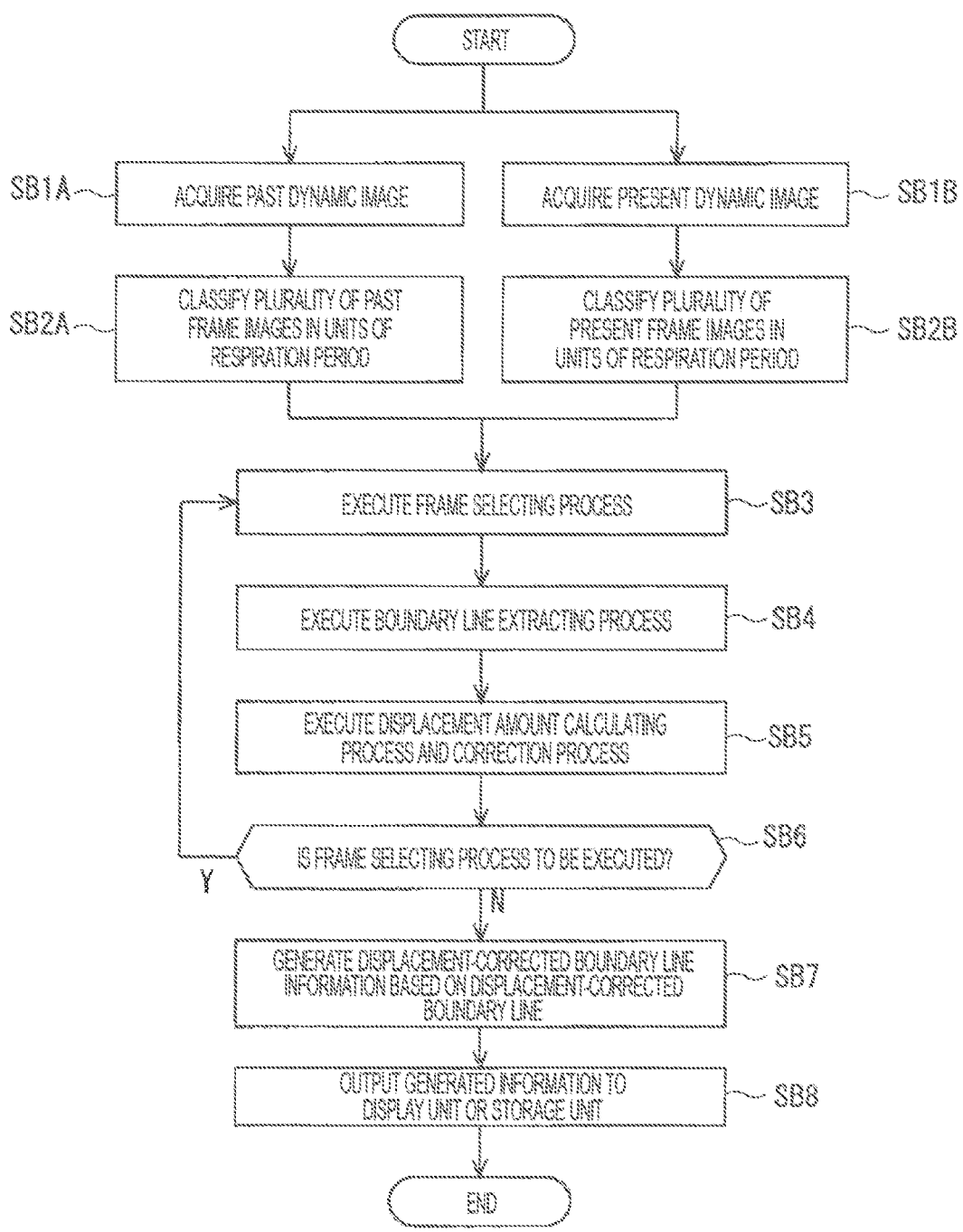
FIG. 28 is a flowchart that illustrates the basic operation of an image processing device 3B realized according to a fifth embodiment.

Subsequently, FIG. 28 is a diagram that illustrates the operation flow of the image processing device 3B according to the fifth embodiment as an example. In this fifth embodiment, the past dynamic image acquiring unit 210, the present dynamic image acquiring unit 310, the present period classifying unit 315, and the past period classifying unit 215, which are not provided in the first embodiment, and the frame selecting unit 120B replaces the frame selecting unit 120, whereby the process is changed as below.

In other words, in Step SB1A, the past dynamic image acquiring unit 210 acquires a past dynamic image (a plurality of past frame images PMI) from the past image storing unit 51 of the information storing device 5.

In Step SB2A, the past period classifying unit 215 classifies a plurality of past frame images PMI in units of the past respiration period PPC, thereby acquiring a plurality of past frame images PMI'. At this time, the past period classifying unit 215 detects the past maximum value PB1 and the past minimum value PB2 of the past respiration vibration value, a past inhalation phase PPH1 and a past exhalation phase PPH2 in addition to the past respiration period PPC.

In addition, in parallel with Steps SB1A and SB2A, Steps SB1B and SB2B are executed. In other words, in Step SB1B, the present dynamic image acquiring unit 310 acquires a present dynamic image (a plurality of present frame images NMI) photographed by the reading control device 14 of the photographing apparatus 1 through the photographing control device 2.

In Step SB2B, the present period classifying unit 315 classifies a plurality of present frame images NMI in units of present respiration periods NPC, thereby acquiring a plurality of present frame image NMI'. At this time, the present period classifying unit 315 simultaneously detects the present maximum value NB1 and the present minimum value NB2 of the present respiration vibration value, the present inhalation phase NPH1, and the present exhalation phase NPH2 in addition to the present respiration period NPC.

In Step SB3, in the frame selecting process executed by the frame selecting unit 120B, one past frame image PMI is selected as the base frame image BF among the selection target frame images TI (two kinds of frame images including the present frame images NMI and the past frame images PMI). The remaining frame selecting process is similar to Step S2. In other words, in the example illustrated in FIG. 27, the past frame image PT1 is selected as the base frame image BF, and the present frame images NT1 to NT5 are selected as the reference frame images RF. In other words, here, the past frame images PT2 to PT5 are excluded from the processing target.

In Step SB4, the boundary line extracting unit 130B executes a process similar to that of the process of Step S3 described above for the past frame image PTI and the present frame image NTI corresponding to the base frame image BF and the reference frame image RF selected in Step SB3, thereby extracting the base boundary line BL and the reference boundary line RL (present diaphragm boundary line NLI).

In Step SB5, the displacement correcting unit 140B appropriately executes a process similar to Step S4 described above for the present diaphragm boundary lines NLI that correspond to the base boundary line BL and the reference boundary line RL extracted in Step SB4, thereby acquiring the present displacement-corrected boundary line NLIc.

In Step SB6, in a case where the displacement correcting unit 140B further executes the process, when the diaphragm boundary line the LI (reference boundary line RL) that is the correction target is changed, the displacement correcting unit 140B instructs the frame selecting unit 120B to change the reference frame image RF, and the process of Steps S3B to S5B is repeated again. On the other hand, in a case where the process is ended by the displacement correcting unit 140B, the process proceeds to Step SB7.

In Step SB7, the image generating unit 150B executes a process similar to Step S6 described above for the present displacement-corrected boundary line NLIc acquired in Step SB4, thereby acquiring the present displacement-corrected boundary line information NLG.

In the present displacement-corrected boundary line information NLG, at least information indicating the present displacement-corrected boundary lines NLIc is included, and it is preferable to also include information indicating the base boundary line BL therein.

Finally, in Step SB8, the image generating unit 150B outputs the present displacement-corrected boundary line information NLG generated in Step SB7 to the display unit 34 or the storage unit 32 (see FIG. 26), and the flow of this operation ends.

As above, according to the image processing device 3B according to the fifth embodiment, the selection target frame images TI include two kinds of frame images (frame images photographed in the past in time with respect to the plurality of frame images) including the present frame image NMI and the past frame image PMI photographed for the same examinee M (body) with the photographing periods thereof being separated far from each other, and the frame selecting process includes a process of selecting a frame image photographed for the same body in the past in time with respect to the plurality of frame images as the base frame image. In other words, in a case where the present displacement-corrected boundary line information NLG indicating the present displacement-corrected boundary lines NLIc is acquired, as the base frame image BF, a common (same) frame image (the past frame image PT1 in the example illustrated in FIG. 27) photographed in the past may be used. Accordingly, through a dynamic-state diagnosis, a comparison between the shapes of the past and the present in the diaphragm boundary line LI of one body and a comparison between changes thereof can be made with high accuracy. For this reason, a follow-up observation can be accurately executed.

<5-8. First Modified Example of Fifth Embodiment: Right and Left Sides of Diaphragm Boundary Line LI>

In the fifth embodiment, in order to display a difference between shape changes of the past and the present of the diaphragm boundary line LI of the examinee M, while the present displacement-corrected boundary line information NLG is acquired, for example, for the purpose of displaying a difference in shape changes of the right and left sides of the diaphragm boundary line LI in the same frame image, right-side displacement-corrected boundary line information and left-side displacement-corrected boundary line information may be acquired (not illustrated in the drawing).

In other words, when the displacement amount calculating process is executed for each of the right and left sides of the diaphragm boundary line LI, as the base boundary line BL, a common (same) right-side diaphragm boundary line (or the left-side diaphragm boundary line) is used. Here, it should be noted that the shapes of the diaphragm boundary lines LI of the right side and the left side have a relation of line symmetry with respect to the spine as its symmetrical axis, and thus, by reversing the shape of anyone of the diaphragm boundary lines LI of the right and left sides, the displacement amount calculating process is executed, and the right-side displacement-corrected boundary line and the left-side displacement-corrected boundary line need to be acquired.

<5-9. Second Modified Example of Fifth Embodiment: Inhalation Phase PH1 and Exhalation Phase PH2>

In a second modified example, for the purpose of displaying a difference in the shape changes at the time of the inhalation phase PH1 of the diaphragm boundary line LI and at the time of the exhalation phase PH2, inhalation displacement-corrected boundary line information and exhalation displacement-corrected boundary line information may be acquired (not illustrated in the drawing).

In other words, when the displacement amount calculating process is executed at the time of the inhalation phase PH1 of the diaphragm boundary line LI and at the time of the exhalation phase PH2, as the base boundary line BL, a common (same) inhalation diaphragm boundary line (or an exhalation diaphragm boundary line) is used, and an inhalation displacement-corrected boundary line and a left-side displacement-corrected boundary line are acquired.

6. Sixth Embodiment

As it is difficult to perceive the motion of the diaphragm area directly from the diaphragm boundary line LI as described above, it is also difficult to perceive the motion of the heart directly from the heart boundary line. In other words, since a motion other than the actual motion of the heart is accompanied, it is difficult to precisely diagnose the motion of the heart.

Thus, while the first to fifth embodiments relate to a case where the target area is the diaphragm area, in a sixth embodiment, a case will be considered in which the target area is the heart area. A difference from the first embodiment is that the boundary line extracting unit 130 is replaced with a boundary line extracting unit 130C that extracts the boundary line of a heart area. In addition, as illustrated in the fourth and fifth embodiments, in a case where the period classifying unit is included, it is replaced with a period classifying unit 115C that classifies a plurality of frame images MI based on a periodical change of the heart. The remaining configuration is similar to that of the image processing device according to one of the first to fifth embodiments.

Like this embodiment, in a case where the target area is the heart area, in addition to the motion of the heart as the motion of the heart at the time of the presence of respiration, the motion of the respiration is accompanied. Thus, even when a correction process is executed through the first displacement amount calculating process in which only the vertical motion is considered, an appropriate displacement-corrected boundary line LIc cannot be acquired. For this reason, a displacement amount D is preferably calculated through the second to fourth displacement amount calculating processes. Alternatively, a method may be used in which, after the displacement amount D of the diaphragm area is removed, the displacement amount D of the heart area is calculated through the first displacement amount calculating process.

Hereinafter, first, the boundary line extracting unit 130C will be described, and then, the period classifying unit 115C will be described.

<6-1. Boundary Line Extracting Unit 130C>

The boundary line extracting unit 130C executes a boundary line extracting process in which a first number of heart boundary lines (target area boundary lines) are acquired by extracting the boundary lines of the heart area for the first number of frame images TI.

As a technique for detecting the heart boundary line (the contour of the heart) from each frame image, various known techniques can be employed, and, for example, a technique for detecting the contour of the heart by matching characteristic points of an X-ray image and characteristics of a hear model by using a model (heart model) representing the shape of the heart (for example, see "Image feature analysis and computer-aided diagnosis in digital radiography: Automated analysis of sizes of heart and lung in chest images", Nobuyuki Nakamori et al., Medical Physics, Volume 17, Issue 3, May, 1990, pp. 342-350) or the like may be employed.

The method of extracting the heart boundary line HLI is not limited to the methods described above, but any other method capable of extracting the heart boundary lines from a dynamic image may be used.

Figure 29A:
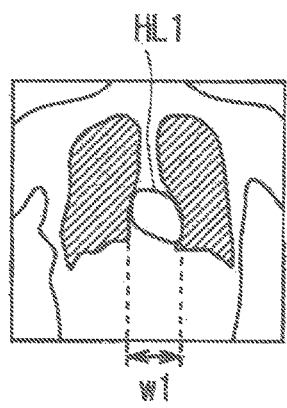
FIG. 29 is a schematic view that illustrates heart boundary lines according to a sixth embodiment.
Figure 29B:
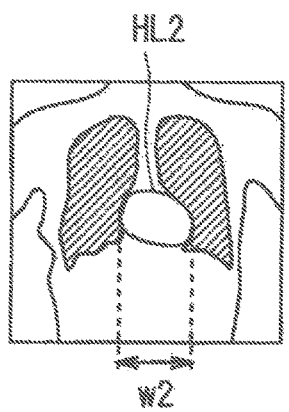
Figure 29C:
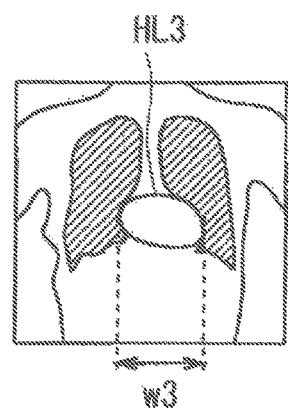

FIG. 29 is a schematic view that illustrates heart boundary lines extracted from each frame image. As illustrated in FIGS. 29A to 29C, it can be understood that heart boundary lines HL1 to HL3 (HLI) are extracted based on each frame image.

<6-2. Period Classifying Unit 115C>

The period classifying unit 115C detects a so-called cardiac cycle (target area period) in which the heart area of an examinee M (body) synchronized with the photographing time, at which a plurality of frame images MI are photographed by the dynamic image acquiring unit 110, periodically changes and classifies the plurality of frame images MI in units of the cardiac cycles. Then, the period classifying unit 115C outputs a plurality of frame images MI' after the classification in units of the cardiac cycles to the frame selecting unit.

Hereinafter, a cardiac cycle acquiring process for detecting the cardiac cycle of the examinee M that is executed by the period classifying unit 115C will be described.

<6-2-1 Cardiac Cycle Acquiring Process>

The cardiac cycle acquiring process is a process for acquiring a heart cycle by calculating the motion amount of the heart wall (in other words, it corresponds to the heart boundary line HLI) by using photographed images acquired by the dynamic image acquiring unit 110. Described in more detail, as a variation in the heart wall is detected from the dynamic image, the phase of the heartbeat is detected at the timing at which each frame image is photographed. Then, the cardiac cycle is determined based on the phase of the heartbeat.

As illustrated in FIG. 29, as an example of the variation of the heart wall (heart boundary line HLI) perceived from the dynamic image, a variation in the horizontal width of the heart will be employed. In other words, in FIGS. 29A to 29C, in the process of expansion of the heart, a state is illustrated as an example in which the horizontal width of the heart increases from w1 to w3.

Thus, from each frame image, by using the method described above or any other method, the contour (heart boundary line HLI) of the heart is detected, and, by detecting the horizontal width of the heart, the cardiac cycle can be detected.

FIG. 30 is an exemplary schematic view that illustrates a relation between photographing time and the horizontal width (the motion amount of the heart wall) of the heart in a plurality of frame images configuring a dynamic image. In FIG. 30, the horizontal axis represents the time, the vertical axis represents the horizontal width of the heart, and each mark represents the value of the detected horizontal width of the heart.

Here, when the horizontal width of the heart acquired at time t is Hwt, and the horizontal width of the heart acquired at time t+1 is Hwt+1, and, in a case where (Hwt+1−Hwt)≥0 is satisfied, a frame image perceived at time t is classified into the expanding time of the heart, and, in a case where (Hwt+1−Hwt)<0 is satisfied, a frame image perceived at time t is classified into the shrinking time of the heart.

In this way, by detecting the horizontal width of the heart, in other words, variations in the heart wall, the time can be classified into the expanding time of the heart or the shrinking time of the heart, and accordingly, the phase of the heart beat can be detected.

As above, the period classifying unit 115C detects the cardiac cycle based on the motion of the heart wall perceived from the dynamic image, whereby a plurality of frame images MI can be classified in units of cardiac cycles.

The cardiac cycle acquiring process may be executed not only by using the method described above but also a method acquiring the cardiac cycle using a result acquired by an electrocardiograph. For example, such a method may be realized by executing a detection operation executed by a phase detecting unit of the electrocardiograph to be synchronized with the imaging operation of the photographing apparatus 1.

As above, the image processing device according to the sixth embodiment has the heart area as the target area and can appropriately diagnose a disease relating to the heart through a dynamic state diagnosis. In the case of a minor symptom, while the abnormality may not be noticed, by making a diagnosis using the displacement-corrected boundary line information LG, the diagnosis does not depend on the user's subjectivity, whereby an erroneous diagnosis can be prevented.

7. Modified Example

As above, while the embodiments of the present invention have been described, the present invention is not limited to the embodiments described above but various changes may be made therein.

Here, while the embodiments are separately illustrated such that the image processing devices 3, 3A, 3B, and the like are individually executed, such individual functions may be combined together as long as there is no contradiction.

Figure 31:
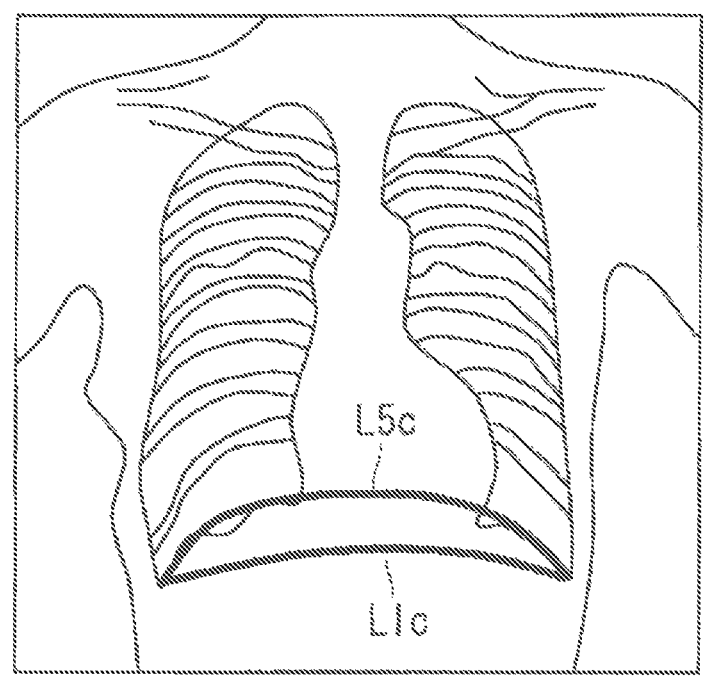
FIG. 31 is a diagram that illustrates an example of a method of displaying displacement-corrected boundary line information.

In the display unit 34 of this embodiment, while the display method illustrated in FIG. 18 has been illustrated, the display method is not limited thereto. For example, the displacement-corrected boundary line information LG of an examinee M determined to be abnormal may be displayed on the dynamic image in an overlapping manner such that a displayed line of the actual dynamic image is indicated. In addition, the displacement-corrected boundary line information LG displayed on the dynamic image may be additionally displayed not only in a case where an abnormality is determined but also before/after the maximum exhalation, the maximum inhalation, or a periodical position at which an occurrence of a disease is suspicious. Furthermore, as illustrated in FIG. 31, when a moving image is reproduced, it may be configured such that the displacement-corrected boundary line L5c corresponding to the maximum exhalation and the displacement-corrected boundary line L1c corresponding to the maximum inhalation are constantly displayed, and the other displacement-corrected boundary lines are not displayed.

While the image processing device 3 according to the first embodiment has been described to be configured to include the frame selecting unit 120, the present invention is not limited thereto, but a configuration not including the frame selecting unit 120 may be employed. In other words, in the configuration not including the frame selecting unit 120, the boundary line extracting unit 130 executes the boundary line extracting process for all of the plurality of frame images MI configuring a dynamic image acquired by the dynamic image acquiring unit 110. Then, the displacement correcting unit 140, under a condition (a predetermined rule) designated by the user in advance, sequentially sets a base boundary line BL and reference boundary lines RL, whereby the displacement amount calculating process and the correction process are executed.

In this embodiment, while the frame selecting process executed by the frame selecting unit 120 is executed as a pre-process of the boundary line extracting process executed by the boundary line extracting unit 130, the present invention is not limited thereto, but the frame selecting process may be configured as a post-process of the boundary line extracting process. In other words, after the boundary line extracting process is executed for all the plurality of frame image MI configuring the dynamic image acquired by the dynamic image acquiring unit 110, in the frame selecting process, the base frame image BF (base boundary line BL) and the reference frame image RF (reference boundary line RL) are selected. In other words, simultaneously with the execution of the frame selecting process, the diaphragm boundary line LI of the base frame image BF is set as the base boundary line BL, and the diaphragm boundary line LI of the reference frame image RF is set as the reference boundary line RL.

While each image processing device according to this embodiment handles cases where the target area is the diaphragm or the heart area, the target area is not limited thereto, and the target area may be the diaphragm area and the heart area. In other words, the process until the displacement-corrected boundary line information LG is acquired is executed parallel for the diaphragm area and the heart area, and the displacement-corrected boundary line information LG is separately output to the display unit 34 and the storage unit 32 for each target area.

In the first modified example of the fifth embodiment, while the purpose is regarded to be the acquisition of the right-side displacement-corrected boundary line and the left-side displacement-corrected boundary line, the purpose is not limited thereto. Thus, for example, for diaphragm boundary lines LI of healthy persons and diaphragm boundary lines LI of unhealthy persons, by executing the process by using a common (same) healthy person diaphragm boundary line as the base boundary line BL, a displacement-corrected boundary line of healthy persons and a displacement-corrected boundary line of unhealthy persons may be acquired.

Here, the subject is not limited to a human body but may be an animal body.

While the present invention has been described in detail, the description presented above is an example in every aspect, and the present invention is not limited thereto. In addition, it is understood that unlimited number of modified examples not illustrated here may be considered without departing from the scope of the present invention.

REFERENCE SIGNS LIST

1 Photographing apparatus
2 Photographing control device
3, 3A, 3B Image processing device
31, 31A, 31B Control unit
Storage unit
Display unit
100 Radiation dynamic image photographing system
110, 110B Dynamic image acquiring unit
115, 115B Period classifying unit
120, 120A, 120B Frame selecting unit
130, 130B Boundary line Extracting unit
140, 140B Displacement Correcting unit
150, 150B Image Generating unit
210 Past dynamic image acquiring unit
215 Past period classifying unit
310 Present dynamic image acquiring unit
315 Present period classifying unit
M Subject (examinee)
MI Frame image
TI First number of frame images
BF Base frame image
RF Reference frame image
BL Base boundary line
RL Reference boundary line
LI Diaphragm boundary line
HLI Heart boundary line
LIc Displacement-corrected boundary line
LG Displacement-corrected boundary line information
PC Respiration Period
PH Respiration Phase
PH1 Inhalation phase
PH2 Exhalation phase
EM Maximum exhalation phase
IM Maximum inhalation phase

The invention claimed is:

1. An image processing device comprising:
a dynamic image acquiring means that acquires a dynamic image configured by a plurality of frame images acquired by sequentially photographing a time-varying physical state of a target area inside a human body or an animal body in a time direction;
a boundary line extracting means that executes a boundary line extracting process in which a plurality of target area boundary lines are acquired by extracting boundary lines of the target area for a plurality of frame images among the plurality of frame images;
a displacement correcting means that acquires a predetermined number of displacement-corrected boundary lines in which a removal-required component is removed by executing a displacement amount calculating process in which a displacement amount, which is the removal-required component, is calculated using a base boundary line as a displacement base for one or more of target area boundary lines other than the base boundary line among the plurality of target area boundary lines by using pixels corresponding to the plurality of target area boundary lines and executing a correction process in which a predetermined number of the target area boundary lines other than the base boundary line are corrected by using the displacement amount after the displacement amount calculating process; and
a display means that displays displacement-corrected boundary line information for display based on the predetermined number of displacement-corrected boundary lines.

2. The image processing device according to claim 1, wherein the removal-required component includes at least one component among deformation components according to a vertical motion, a parallel motion, and rotation in the target area.

3. The image processing device according to claim 1, further comprising a frame selecting means that executes a frame selecting process including a process of selecting a base frame image used for extracting the base boundary line and a reference frame image used for extracting the target area boundary lines other than the base boundary line for selection target frame images including at least the plurality of frame images,
  wherein the displacement amount calculating process includes a process of calculating a displacement amount between corresponding pixels of the target area boundary line of the base frame image as the base boundary line and the target area boundary line of the reference frame image.

4. The image processing device according to claim 3, wherein the selection target frame images include frame images photographed in the past in time with respect to the plurality of frame images, and
  the frame selecting process includes a process of selecting a frame image photographed for the same body in the past in time with respect to the plurality of frame images as the base frame image.

5. The image processing device according to claim 3, further comprising a period classifying means that detects a target area period in which a periodical change of the target area of the body synchronized with photographing time at which the plurality of frame images are photographed occurs and classifies the plurality of frame images in units of the target area periods,
  wherein the base frame image and the reference frame image are frame images when the target area periods are within a same period,
  a value representing a time-varying physical state of the target area is defined as a physical state value, and
  the frame selecting process includes a first selection process selecting one frame image as the base frame image from among
  (b1) a frame image when the physical state value corresponds to a first set value set in advance,
  (b2) a frame image when the physical state value corresponds to a maximum value, and
  (b3) a frame image when the physical state value corresponds to a minimum value, and
  a second selection process selecting one frame image as the reference frame image from among
  (c1) a frame image when the physical state value corresponds to a second set value set in advance,
  (c2) a frame image that is adjacent to the base frame image in time,
  (c3) a frame image corresponding to the minimum value of the physical state value when the base frame image is the frame image of (b2), and
  (c4) a frame image corresponding to the maximum value of the physical state value when the base frame image is the frame image of (b3).

6. The image processing device according to claim 3, wherein the displacement amount used for the correction process is a displacement amount between corresponding pixels of the base boundary line and one of the target area boundary lines, and the target area boundary lines other than one of the target area boundary lines are corrected using the displacement amount.

7. The image processing device according to claim 3, wherein the displacement amount used for the correction process is a displacement amount from the target area boundary line nearest in time from the target area boundary line that is a correction target.

8. The image processing device according to claim 3, wherein the displacement amount used for the correction process is a displacement amount between the base boundary line and the target area boundary line, which is the correction target, that is acquired as a sum of displacement amounts of two boundary lines adjacent in time.

9. The image processing device according to claim 1, further comprising an image generating means that generates a predetermined number of separate images separated for each predetermined number of displacement-corrected boundary lines,
  wherein the display means sequentially displays the predetermined number of separate images as displacement-corrected boundary line information.

10. The image processing device according to claim 1, further comprising an image generating means that generates one still image such that the plurality of displacement-corrected boundary lines are displayed in an overlapping manner,
  wherein the display means displays the still image as the displacement-corrected boundary line information.

11. The image processing device according to claim 1, wherein the target area includes at least one of a diaphragm area and a heart area.

12. A non-transitory recording medium storing a computer readable program that causes a computer to serve as the image processing device according to claim 1 by being executed by the computer included in the image processing device.

13. The image processing device according to claim 2, further comprising a frame selecting means that executes a frame selecting process including a process of selecting a base frame image used for extracting the base boundary line and a reference frame image used for extracting the target area boundary lines other than the base boundary line for selection target frame images including at least the plurality of frame images,
  wherein the displacement amount calculating process includes a process of calculating a displacement amount between corresponding pixels of the target area boundary line of the base frame image as the base boundary line and the target area boundary line of the reference frame image.

14. The image processing device according to claim 2, further comprising an image generating means that generates a predetermined number of separate images separated for each predetermined number of displacement-corrected boundary lines,
  wherein the display means sequentially displays the predetermined number of separate images as displacement-corrected boundary line information.

15. The image processing device according to claim 2, further comprising an image generating means that generates one still image such that the plurality of displacement-corrected boundary lines are displayed in an overlapping manner,
  wherein the display means displays the still image as the displacement-corrected boundary line information.

16. The image processing device according to claim 2, wherein the target area includes at least one of a diaphragm area and a heart area.

17. A non-transitory recording medium storing a computer readable program that causes a computer to serve as the image processing device according to claim 2 by being executed by the computer included in the image processing device.

18. The image processing device according to claim 3, further comprising an image generating means that generates a predetermined number of separate images separated for each predetermined number of displacement-corrected boundary lines,
    wherein the display means sequentially displays the predetermined number of separate images as displacement-corrected boundary line information.

19. The image processing device according to claim 3, further comprising an image generating means that generates one still image such that the plurality of displacement-corrected boundary lines are displayed in an overlapping manner,
    wherein the display means displays the still image as the displacement-corrected boundary line information.

20. The image processing device according to claim 3, wherein the target area includes at least one of a diaphragm area and a heart area.

* * * * *